(12) United States Patent
Fiering et al.

(10) Patent No.: US 10,987,462 B2
(45) Date of Patent: Apr. 27, 2021

(54) ACOUSTOPHORESIS DEVICE HAVING IMPROVED DIMENSIONS

(71) Applicant: The Charles Stark Draper Laboratory, Inc., Cambridge, MA (US)

(72) Inventors: Jason Fiering, Boston (MA); Ryan Silva, Medford, MA (US); Parker Stewart Dow, Boston, MA (US)

(73) Assignee: The Charles Stark Draper Laboratory, Inc., Cambridge, MA (US)

(*) Notice: Subject to any disclaimer, the term of this patent is extended or adjusted under 35 U.S.C. 154(b) by 160 days.

(21) Appl. No.: 16/008,780

(22) Filed: Jun. 14, 2018

(65) Prior Publication Data

US 2018/0361053 A1 Dec. 20, 2018

Related U.S. Application Data

(60) Provisional application No. 62/519,630, filed on Jun. 14, 2017.

(51) Int. Cl.
*A61M 1/00* (2006.01)
*A61M 1/14* (2006.01)
(Continued)

(52) U.S. Cl.
CPC ........ *A61M 1/3678* (2014.02); *A61M 1/1621* (2014.02); *A61M 1/362* (2014.02);
(Continued)

(58) Field of Classification Search
CPC .... B01L 3/00; B01L 3/50; B01L 3/502; B01L 3/5027; B01L 3/502707; B01L 3/50273; B01L 3/502753; B01L 2200/00; B01L 2200/06; B01L 2200/0631; B01L 2200/0647; B01L 2200/0652; B01L 2200/12; B01L 2300/00; B01L 2300/08; B01L 2300/0832; B01L 2300/0861; B01L 2300/16; B01L 2400/00; B01L 2400/04; B01L 2400/0403; B01L 2400/0433;
(Continued)

(56) References Cited

U.S. PATENT DOCUMENTS 9,504,780 B2 * 11/2016 Spain .................. A61M 1/3693
9,731,062 B2 * 8/2017 Fiering ............... A61M 1/3693
(Continued)

FOREIGN PATENT DOCUMENTS

WO WO-2015/100028 7/2015
WO WO-2016/177832 11/2016

OTHER PUBLICATIONS

International Search Report and Written Opinion for PCT/US2018/037568 dated Aug. 8, 2018.

*Primary Examiner* — Natasha E Young
(74) *Attorney, Agent, or Firm* — Foley & Lardner LLP

(57) ABSTRACT

Systems and methods for cleansing blood are disclosed herein. The methods include acoustically separating target particles from elements of whole blood. The whole blood and capture particles are flowed through a microfluidic separation channel formed in a thermoplastic. At least one bulk acoustic transducer is attached to the microfluidic separation channel. A standing acoustic wave, imparted on the channel and its contents by the bulk acoustic transducer, drives the formed elements of the blood and target particles to specific aggregation axes.

18 Claims, 14 Drawing Sheets

(51) Int. Cl.
| | |
|---|---|
| *A61M 1/16* | (2006.01) |
| *A61M 1/36* | (2006.01) |
| *B01L 3/00* | (2006.01) |
| *G01N 33/00* | (2006.01) |
| *G01N 33/48* | (2006.01) |
| *G01N 33/49* | (2006.01) |
| *B01D 21/00* | (2006.01) |
| *B01D 21/28* | (2006.01) |

(52) U.S. Cl.
CPC ......... *A61M 1/3639* (2013.01); *B01D 21/283* (2013.01); *B01L 3/5027* (2013.01); *B01L 3/50273* (2013.01); *B01L 3/502707* (2013.01); *B01L 3/502753* (2013.01); *A61M 1/3672* (2013.01); *A61M 2202/0411* (2013.01); *A61M 2202/08* (2013.01); *A61M 2205/36* (2013.01); *B01D 2221/10* (2013.01); *B01L 2200/0631* (2013.01); *B01L 2200/0652* (2013.01); *B01L 2200/12* (2013.01); *B01L 2300/08* (2013.01); *B01L 2300/0832* (2013.01); *B01L 2300/0861* (2013.01); *B01L 2300/16* (2013.01); *B01L 2400/0436* (2013.01); *B01L 2400/0496* (2013.01); *G01N 33/491* (2013.01)

(58) Field of Classification Search
CPC ..... B01L 2400/0436; B01L 2400/0493; B01L 2400/049; A61M 1/00; A61M 1/14; A61M 1/16; A61M 1/1621; A61M 1/36; A61M 1/362; A61M 1/3621; A61M 1/3639; A61M 1/3672; A61M 1/3678; A61M 2202/00; A61M 2202/04; A61M 2202/0405; A61M 2202/0407; A61M 2202/0411; A61M 2202/08; A61M 2205/00; A61M 2205/36; G01N 33/00; G01N 33/48; G01N 33/483; G01N 33/487; G01N 33/49; G01N 33/491; B01D 21/00; B01D 21/28; B01D 21/283; B01D 2221/00; B01D 2221/10
See application file for complete search history.

(56) References Cited

U.S. PATENT DOCUMENTS

| | | | |
|---|---|---|---|
| 2014/0209542 A1* | 7/2014 | Spain | A61M 1/3693 210/690 |
| 2018/0313816 A1* | 11/2018 | Fiering | B01L 3/502753 |
| 2019/0290829 A1* | 9/2019 | Fiering | C12N 5/0641 |
| 2019/0388606 A1* | 12/2019 | Fiering | A61M 1/3693 |

* cited by examiner

ACOUSTOPHORESIS DEVICE HAVING IMPROVED DIMENSIONS

CROSS-REFERENCE TO RELATED APPLICATIONS

This application claims priority to U.S. Provisional Patent Application No. 62/519,630 filed on Jun. 14, 2017, which is herein incorporated by reference in its entirety.

BACKGROUND OF THE DISCLOSURE

Sepsis is a disease with a very significant public health impact that has stubbornly resisted new therapies. Antibiotics are the only real therapeutic option, yet sepsis can be caused by over 100 bacteria and many fungi, so a universal antibiotic is not a realistic option; the antibiotics and antifungals used have significant complications and are often unsuitable for fragile patients. The concept of cleansing the blood has been tried previously without success. Previous blood cleansing concepts have included laboratory scale methods of centrifugation, capillary electrophoresis, liquid chromatography, field flow fractionation, and liquid-liquid extraction. These devices have failed to deliver continuous flow cleansing devices. In addition to often discarding large portions of the blood, current cleansing devices may rely on diluents, sheath flow, controlled solution conductivity, costly microfabricated on-chip materials, and toxic additives.

SUMMARY OF THE DISCLOSURE

The present disclosure described new design rules for plastic-based devices. Specifically, the disclosure describes ratios between operation frequency, wall thickness, and channel width that can be used to calculate optimized channel dimensions for separation devices constructed in plastic.

Silicon, glass, or metal devices are commonly used for acoustophoresis because the rigid channel walls provide a near ideal acoustic boundary against the sample fluid, enhancing the required standing wave resonance. This ideal boundary simplifies design because the resultant reduction in mathematical complexity allows for the development of models that can be used to calculate the resonant modes in the channel-fluid system. However, the rigid materials previously used are expensive and slow to manufacture, have poor compatibility with many biological samples, and are unlikely to be acceptable for mass production of disposable laboratory tools.

According to at least one aspect of the disclosure, a cleansing device can include a first thermoplastic substrate. The substrate can include a separation channel having a width, a first wall, a second wall, and a floor. The floor can be configured to couple with an acoustic transducer and a thickness of the first wall and the second wall can be based on the width of the separation channel. The device can include a first inlet configured to introduce a fluid into a proximal end portion of the separation channel. The device can include a first outlet at the downstream portion of the separation channel positioned substantially along the longitudinal axis of the separation channel. The device can include a second outlet at the downstream portion positioned adjacent a first wall of the separation channel. The device can include a second thermoplastic substrate coupled with the first thermoplastic substrate and defining a roof of the separation channel.

In some implementations, the thickness of the floor can be based on the width of the separation channel. The width of the separation channel can be between 0.1 mm and 3 mm. The thickness of the first wall and second wall can be based on a velocity of an acoustic wave through the fluid. The thickness of the first wall and the second wall can be based on a velocity of the acoustic wave through the first thermoplastic substrate. The height of the separation channel can be based on the width of the separation channel.

In some implementations, a ratio of the separation channel to the height of the separation channel can be between 2 and 2.5. The floor of the separation channel can have a first thickness and the roof of the separation channel can have a second thickness. The first thickness can be greater than the second thickness. A ratio of the thickness of the floor of the separation channel to a width of the separation channel can be between about 0.5 and 1.

According to at least one aspect of the disclosure, a method to cleanse fluid can include providing a separation device. The device can include a first thermoplastic substrate that can include a separation channel having a width, a first wall, a second wall, and a floor. The floor can be configured to couple with an acoustic transducer and a thickness of the first wall and the second wall can be based on the width of the separation channel. The device can include a first inlet configured to introduce a fluid into a proximal end portion of the separation channel. The device can include a first outlet at the downstream portion of the separation channel positioned substantially along the longitudinal axis of the separation channel. The device can include a second outlet at the downstream portion positioned adjacent a first wall of the separation channel. The device can include a second thermoplastic substrate coupled with the first thermoplastic substrate and defining a roof of the separation channel. The method can include flowing a fluid through the first inlet. The fluid can include undesirable particles. The method can include driving, with a standing acoustic wave generated by the acoustic transducer, the undesirable particles toward the first wall of the separation channel.

In some implementations, the method can include applying the standing acoustic wave through the floor of the separation channel. The width of the separation channel can be between 0.1 mm and 3 mm. The thickness of the first wall and second wall can be based on a velocity of the acoustic wave through the fluid and a velocity of the acoustic wave through the first wall and the second wall. The thickness of the first wall and the second wall can be based on a velocity of the acoustic wave through the first thermoplastic substrate. The height of the separation channel can be based on the width of the separation channel.

In some implementations, a ratio of the separation channel to the height of the separation channel can be between 2 and 2.5. The floor of the separation channel can have a first thickness and the roof of the separation channel can have a second thickness. The first thickness can be greater than the second thickness. A ratio of the thickness of the floor of the separation channel to a width of the separation channel can be between about 0.5 and 1.

The present disclosure discusses design rules for the manufacture of separation channels in plastic, including thermoplastics and other lossy plastics. While acoustic separation devices can be constructed in plastic using the same design rules for silicon, glass, or metal devices, the design rules do not provide optimized, plastic-based devices because the simplified analysis no longer applies since the channel walls can no longer be considered ideally rigid.

BRIEF DESCRIPTION OF THE DRAWINGS

The skilled artisan will understand that the FIGS., described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION OF THE PREFERRED EMBODIMENTS

The various concepts introduced above and discussed in greater detail below may be implemented in any of numerous ways, as the described concepts are not limited to any particular manner of implementation. Examples of specific implementations and applications are provided primarily for illustrative purposes.

The present system and methods described herein generally relate to a system for cleansing blood. Accordingly, in various implementations, the disclosure relates to the acoustically separating particles from the blood (or other fluids) via high throughput microfluidic arrays. The separated particles can generally be referred to as target particles. The target particles can be undesirable particles in cases where the devices described herein are used for purification or filtering. In other implementations, the target particles can be cells or particles that are removed from a fluid for further study or processing (e.g., the target particles are desired particles). For example, the target particles can be cells that are removed from a fluid such that a diagnostic analysis can be performed on the cells. In certain implementations, in part to overcome the prior deficiencies with the poor performance of acoustic separation on small particles, prior to acoustic separation of the blood, capture particles are introduced and mixed with the blood to form complexes with the undesirable particles, yielding particles large enough to be effectively and efficiently targeted by acoustic separation.

Figure 1:
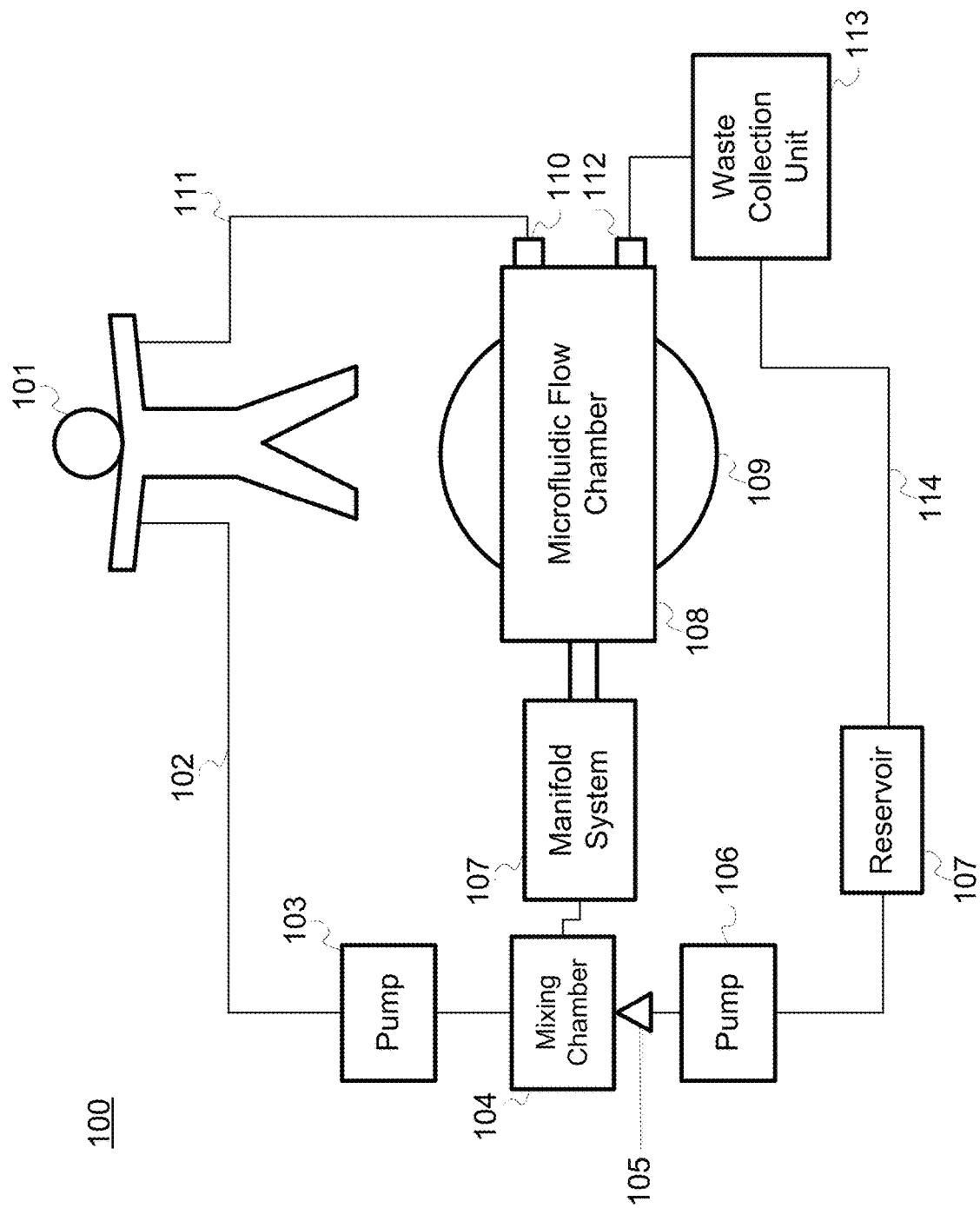
FIG. 1 is a block diagram of an example system for cleansing blood.

FIG. 1 illustrates a system 100 for cleansing blood by removing waste material such as bacteria, viruses and toxins. In the system 100, blood is removed from a patient via an intravenous line 102. The blood is then pumped to a mixing chamber 104 by a first pump 103. In the mixing chamber 104, capture particles are mixed with whole blood. The components of the capture particles are stored in a reservoir 107. From the reservoir 107, the capture particles are pumped by a second pump 106 into the mixing chamber. The capture particles are formed as the contents of the reservoir 107 are extruded from a micronozzle 105 at the entrance to the mixing chamber 104. From the mixing chamber 104, the whole blood and capture particles enter a manifold system 107. The manifold system 107 distributes the whole blood and capture particles to a plurality of separation channels contained within the microfluidic flow chamber 108. The microfluidic flow chamber 108 sits atop at least one bulk piezoelectric acoustic transducer 109. The acoustic waves generated by the bulk piezoelectric acoustic transducers are used to funnel the contents of the whole blood and capture particles to specific outlets of the separation channels. As the whole blood flows through the microfluidic flow chamber 108, cleansed blood flows to a first outlet 110. After exiting the first outlet 100, the cleansed blood returns to the patient 101 via a second intravenous line 111. The capture particles and other waste material removed from the blood exit the microfluidic flow chamber 108 via a second outlet 112. Next, the waste material and capture particles enter a waste collection unit 113. In the waste collection unit 113, the capture particles are separated from the waste material. Once separated, the waste material is discarded, and the capture particles are returned to the reservoir 107 by tubing 114. Once returned to the reservoir 107, the capture particles are reused in the system to remove additional waste material from whole blood as it continues to flow through the system.

The system 100, as illustrated, includes a pump 103 for moving blood from the patient 101 to the mixing chamber 104. In some implementations, the pump operates continuously, while in other implementations the pump works intermittently and only activates when the level of whole blood in the mixing chamber 104 or manifold falls below a set threshold. In some implementations, the flow rate of the pump is configurable, such that the rate the blood exits the patient can be configured to be faster or slower than if no pump was used. In yet other implementations, no external pump is required. In this example, the blood is transported to the mixing chamber 104 by the pressure generated by the patient's own heart. In some implementations, the patient 101 is connected to a blood pressure monitor, which in turn controls the pump. Example pumps can include, but are not limited, to peristaltic pumps or any other pump suitable for flowing blood.

As illustrated in the system 100, capture particles are also pumped into the mixing chamber. A second pump 106 pumps the ingredients to form the capture particles from a reservoir 107 to the mixing chamber 104. In some implementations, the components of the capture particles are continuously agitated in the reservoir 107 in order to keep the components well mixed. The components are formed into capture particles as they enter the mixing chamber 104. The components enter the mixing chamber 104 through a micronozzle 105. In some implementations, the micronozzle 105 injects the capture particles into the mixing chamber 104. In other implementations, the micronozzle 105 injects the capture particles into the manifold system 107, and in yet other implementations the micronozzle 105 is positioned such that it injects capture particles directly into the separation channels of the microfluidic chamber 108. In some implementations, the micronozzle 105 is a micro-machined nozzle, configured to allow a specific amount of the capture particle components through the nozzle at a given time. In some implementations, the micronozzle is an array of micronozzles. In yet other implementations, the micronozzle is a membrane with pores. The pump 106 is configured to flow the contents of the reservoir through the micronozzle 105 at a predetermined rate such that the amphipathic characteristics of the molecules of the components of the captures particles cause the capture particles to spontaneously form as they exit the micronozzle 105.

In some implementations, a micronozzle is not used to generate the capture particles. In these implementations, the capture particles are premade. The capture particles are then stored in the reservoir and introduced into the system by the pump 106 at either the mixing chamber 104, manifold system 107, and/or the separation channels of the microfluidic flow chamber 108. In some implementations, capture particles are not used. The particles of the fluid can be driven to an aggregations axis based on the particle's inherent acoustic contrast factor with respect to the fluid.

As illustrated in system 100, the whole blood containing target particles and the capture particles enter the mixing chamber 104. In some implementations, the contents of the mixing chamber are continuously agitated to improve distribution of the capture particles throughout the whole blood and target particles such that the capture particles bind to the target particles. In some implementations, anticoagulants or blood thinners are introduced into the mixing chamber 104 to assist the blood as it flows through the system 100. In some implementations, the mixing chamber 104 contains a heating element for warming the contents of the mixing chamber 104.

The contents of the mixing chamber 104 then flow into the manifold system 107, as illustrated by system 100. The manifold system 107 flows the whole blood, target particles, and capture particles into the inlets of the plurality of separation channels of the microfluidic flow chamber 108.

In the illustrated system 100, the microfluidic flow chamber 108 contains a plurality of separation channels. The capture particles and target particles are driven with standing acoustic waves to outlets. In some implementations, the separation occurs during a single stage, while in other implementations, the separation occurs over a plurality of stages. In some implementations, the microfluidic flow chamber is disposable.

As shown in the illustrations of system 100, the microfluidic flow chamber 108 sits atop a bulk piezoelectric acoustic transducer 109. In some implementations, the system 100 contains a single bulk piezoelectric acoustic transducer 109, while in other implementations the system 100 contains a plurality of bulk piezoelectric acoustic transducers 109.

In some implementations, the bulk piezoelectric acoustic transducer 109 is glued to the microfluidic flow chamber 108. In other implementations, the microfluidic flow chamber 108 is clamped to the bulk piezoelectric acoustic transducer 109 so the microfluidic flow chamber may easily be removed from the system. In other implementations, the adhesive material connecting the bulk piezoelectric acoustic transducer 109 to the microfluidic flow chamber 108 is removable, for example by heating the adhesive.

The bulk piezoelectric acoustic transducer 109 imposes a standing acoustic wave on the separation channels of the microfluidic flow chamber 108 transverse to the flow of the fluid within the microfluidic flow chamber 108. The standing acoustic waves are used to drive fluid constituents towards or away from the walls of the separation channels or other aggregation axes.

More particularly, the dimensions of the separation channels are selected based on the wavelength of the imposed standing wave such that a pressure node exists at about the center or other interior axis of the separating channel, while antinodes exist at about the walls of the separation channel. The dimensions are discussed in relation to FIG. 4A. Particles are driven to different positions within the channel based on the sign of their acoustic contrast factor at a rate which is proportional to the magnitude of their contrast factor. Particles with a positive contrast factor (e.g. the formed elements of blood) are driven towards the pressure node within the interior of the separation channel. In contrast, particles with a negative contrast factor are driven toward the pressure antinodes. These principles are depicted and described further in relation to FIGS. 5A and 5B.

Based on these principles, formed elements of blood can be separated from capture particles and the target particles bound to the capture particles. In one way, as described further in relation to FIGS. 2 and 10, capture particles are selected to have negative contrast factors, which is opposite to the positive contrast factors of the formed elements of blood. Thus, in response to the standing acoustic wave, the formed elements are driven towards the resulting pressure node while the capture particles are driven towards the antinodes.

Figure 2:
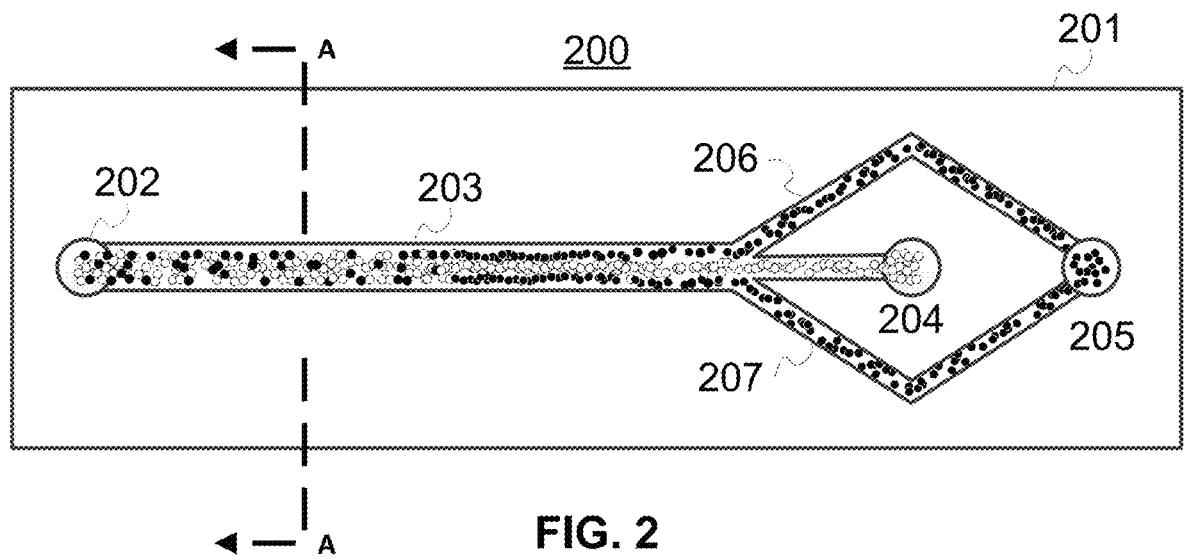
FIG. 2 is a top view of an example single-stage separation channel, such as can be used in the system of FIG. 1.

This technique can be used in a single-stage separation system, as illustrated in FIG. 2. As whole blood and target particles (and in some implementations, capture particles)

mix in the mixing chamber 104 and continue to mix as flowing through the manifold system 107, the target particles enter the area of the separation channel where the standing acoustic wave is imparted. The standing acoustic wave drives the bound target particles to a specific axis (e.g., against the wall of the separation channel) and the formed elements of the whole blood to a second axis (e.g., the middle of the separation channel). Thus, the target particles can be collected from the edges of the separation channel and disposed of while the cleaned blood is collected and returned to the patient.

As illustrated in the system 100, the cleansed blood exits the microfluidic flow chamber 108 at a first outlet 110. From there the blood is returned to the patient 101 via an intravenous supply line 111. In some implementations, the blood in the supply line 111 is reheated to body temperature before returning to the patient 101. In other implementations, an infusion pump is used to return the blood to the patient 101, while in the system 100 the pressure generated in the system by pumps 103 and 106 is adequate to force the blood to return to the patient 101.

As illustrated in the system 100, waste material (e.g. the capture particle and target particles) exits the microfluidic flow chamber 108 and enters a waste collection unit 113. In some implementations, the waste collection unit 113 contains a capture particle recycler. The capture particle recycler unbinds the target particles from the capture particles. The capture particles are then returned to the reservoir 107 via tubing 114. The target particles are then disposed of. In some implementations, the target particles are saved for further testing.

While the system 100 is described above for the in-line cleansing of a patient's blood, in alternative implementations, the system 100 can be used to cleanse stored blood. For example, the system 100 can be used to cleanse collected blood for later infusion to help ensure the safety of the blood.

FIG. 2 illustrates an example single-stage separation channel suitable for use within the microfluidic flow chamber 108 of the blood cleansing system 100. The separation channel includes an inlet 202, a flow channel 203, a first outlet 204, a first outlet channel 206, a second outlet channel 207, and a second outlet 205. The separation channel is manufactured in a sheet of material 201.

In FIG. 2, whole blood, target particles, and capture particles enter the separation channel at the inlet 202 from the manifold system 107. The whole blood, target particles, and capture particles then flow the length of the flow channel 203. The flow channel is subdivided into three regions: an upstream region, a downstream region, and a migration region. The migration region lies between the upstream and downstream regions, and is the region of the flow channel where the standing acoustic wave is imparted transverse to the flow of particles. As the formed elements of the whole blood, capture particles, and the target particles enter the migration region, the standing acoustic wave drives the capture particles bound to the target particles to the side walls of the separation channel, and the formed elements of the whole blood to the center of the channel. The formed elements of the whole blood then exit the separation channel through the outlet 204 located at about the central axis of the separation channel. The capture particles and target particles then exit the separation channel through the first and second outlet channels 206 and 207 which terminate in the second outlet 205. In some implementations, the formed elements are driven to the walls of the separation channel and the capture and target particles remain in the center of the separation channel.

In some implementations, the separation channel 200 can separate target particles from any fluid. As discussed above and later in relation to FIGS. 5 and 7, the separation channel 200 can be used to remove target particles from any fluid, so long as the characteristics of the capture particle are appropriately selected. For example, selecting an encapsulated fluid such that its density and bulk modulus gives the capture particle a contrast factor that distinguishes it from the fluid and other particles in the fluid. For example, the separation channel 200 may be used to remove target particles from, but not limited to, blood plasma, blood serum, water, liquid food products (e.g., milk), lymph, urine, sputum, and cell culture media.

In the implementation of FIG. 2, the outlet 205 is formed from the merging of two outlet channels 206 and 207. In some implementations, the streams do not rejoin but lead to separate outlet terminals.

In FIG. 2, the particles are separated in the same plane as the sheet of material 201 (i.e. particles are aligned to the left, right, or center of the channel); however, in other implementations, the particles are separated out of plane. For example, in some implementations, the particles are aligned with the top, middle, or bottom of the channel.

In FIG. 2, the sheet of material 201 can include thermoplastics or other lossy plastics, such as, but not limited to, polystyrene, acrylic (polymethylmethacrylate), polysulfone, polycarbonate, polyethylene, polypropylene, cyclic olefin copolymer, silicone, liquid crystal polymer, polyimide, polyetherimide, and polyvinylidene fluoride. The channel can be manufactured by a number of manufacturing techniques, including, but not limited to, milling, molding, embossing, and etching.

Figure 3:
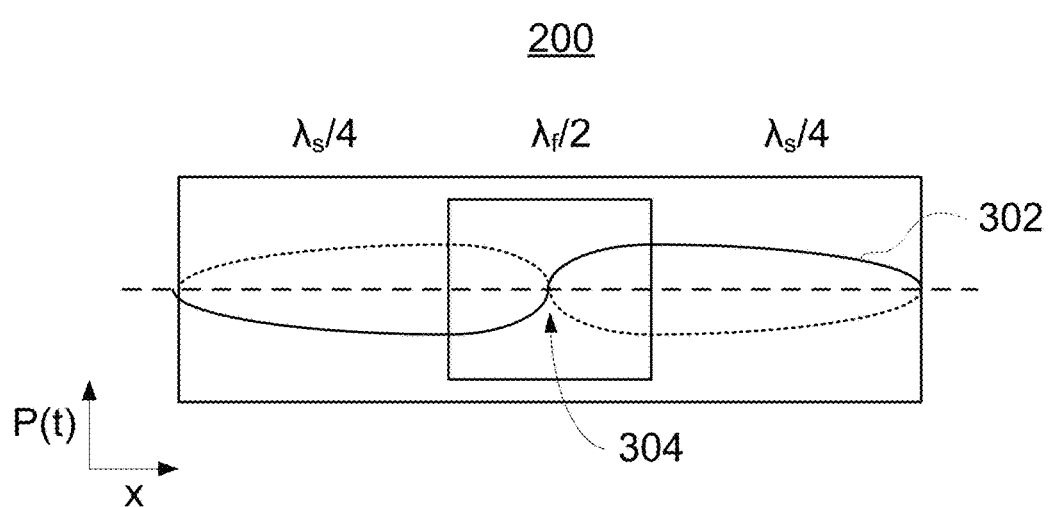
FIG. 3 illustrates a cross sectional view through section A illustrated in FIG. 2.

FIG. 3 illustrates a cross sectional view 300 through section A illustrated in FIG. 2. The wave 302 indicates the pressure amplitude P(t) in a standing wave across the separation channel 200. The solid line and dashed line are alternate phases of the wave 302. Particles accumulate at the pressure node 304 where time averaged P is zero. The frequency and relative dimensions of fluid and walls can be selected as fractions of the acoustic wavelength.

Figure 4A:
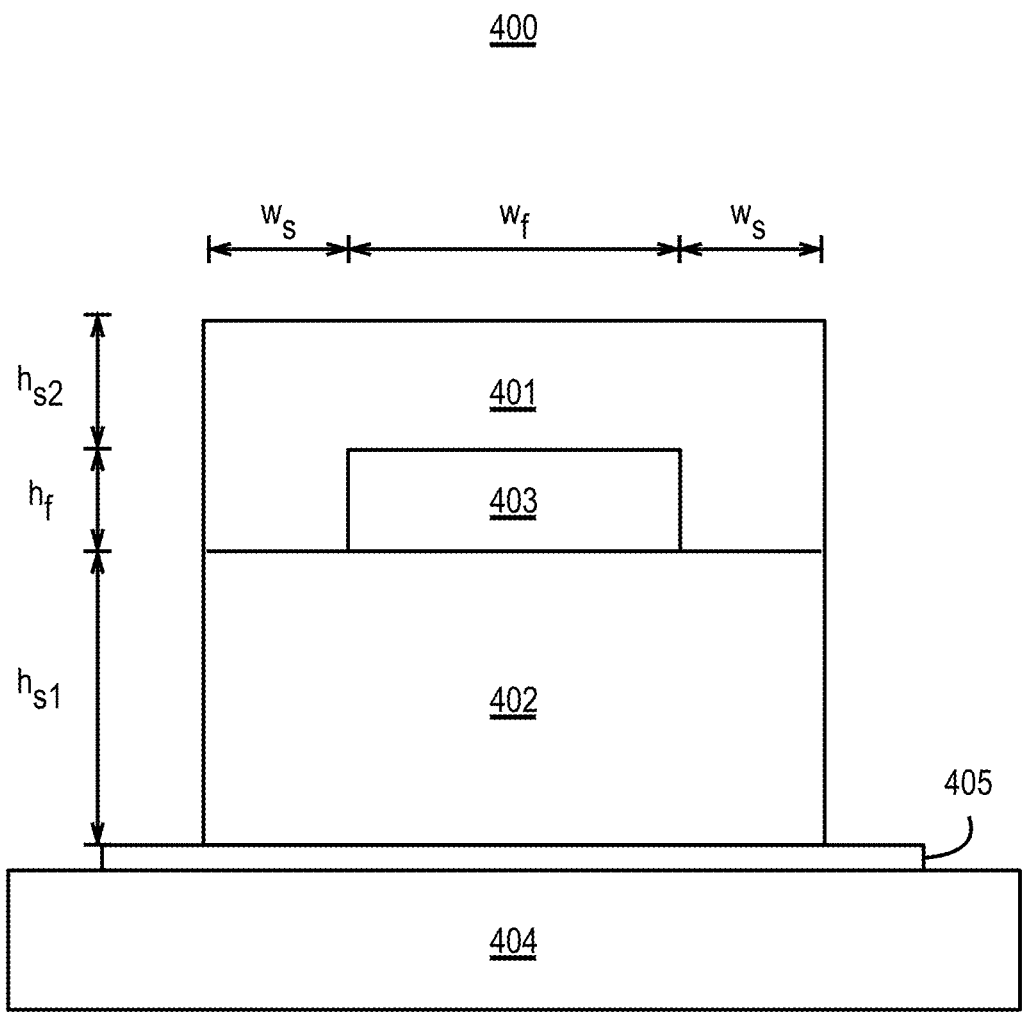
FIG. 4A is a cross sectional view of an example single-stage separation device, such as the separation device of FIG. 2, mounted to a bulk transducer.

FIG. 4A is an illustrative cross-section of a separation device 400 similar to the separation channel depicted in FIG. 2, for example. The separation device 400 includes a top layer 401 sitting atop a bottom layer 402. A separation channel 403 (which can also be referred to as a lumen 403) is formed in the top layer 401. In some implementations, the separation channel 403 is formed in the bottom layer 402 or a combination of the top layer 401 and the bottom layer 402. The bottom layer 402 can form one wall of the separation channel 403, such as the floor of the separation channel 403. The floor of the separation device 400 is coupled with a bulk piezoelectric transducer 404. The wall or portion of material separating the separation channel 403 from the transducer 404 can be referred to as the "floor" and does not have to be the bottom wall of the separation channel. The "ceiling" is the wall opposite the floor. For example, if the transducer were coupled with the top layer 401, the floor would form the top wall (as illustrated in FIG. 4A) of the separation channel 403 and the ceiling would form the bottom wall of the separation channel 403. The separation device 400 is secured to the bulk transducer 404, by a coupling adhesive 405 and/or mechanical clamp. In some implementations, the coupling adhesive is cyanoacrylate glue. In some implementations, the bulk piezoelectric transducer 404 can be operated at a frequency between about 0.5 MHz and about 2.5 MHz, or between about 0.5 MHz and about 1 MHz.

The bottom layer 402 and top layer 401 of the separation device 400 are manufactured from a substrate sheet. The substrate sheet can be made of, without limitation, one of the above described plastics. In some implementations, the bottom layer 402 is manufactured by milling, embossing, molding, and/or etching. After creating the two layers, they can be joined together by thermocompression, mechanical clamping, adhesive bonding, and/or plasma bonding. The separation device can sit atop the acoustic bulk transducer 404 such that the transducer 404 is separated from the separation channel 403 by a distance of $h_{s1}$. For example, the separation channel 403 can have a floor with a thickness of $h_{s1}$. In some implementations, the transducer 404 may be mounted to a sidewall of the separation device 400 such that the transducer 404 is separated from the separation channel 403 by a distance of $w_s$. The transducer 404 imparts a standing acoustic wave of a specific wavelength through the bottom layer 402, separation channel 403, and top layer 401. The dimensions of the bottom layer 402, top layer 401, and separation channel 403 are dependent on the selected wavelength.

Figure 4B:
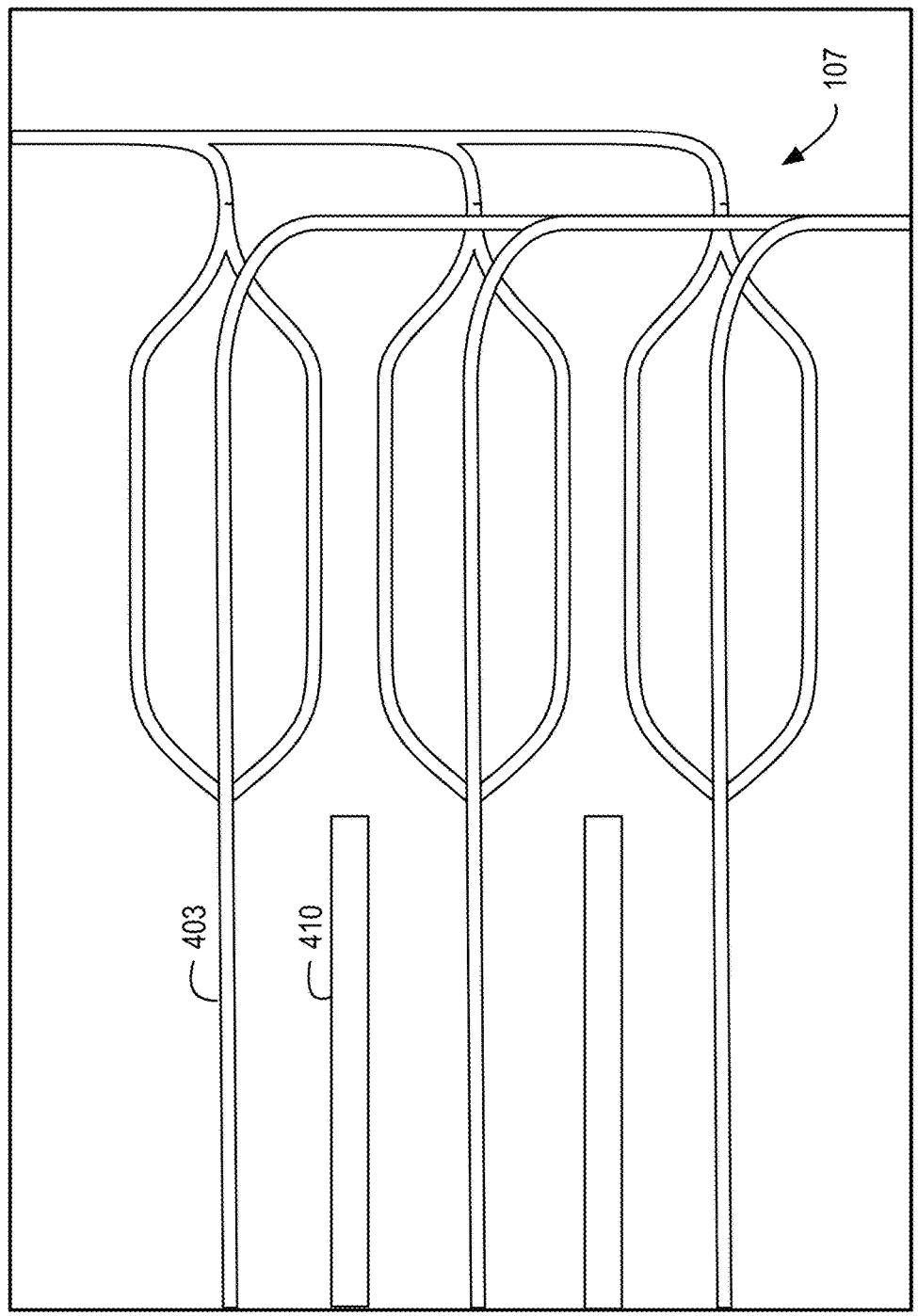
FIG. 4B illustrates a top view of an example separation device with multiple separation channels.

In some implementations, the separation device 400 can include a plurality of separation channels 403. FIG. 4B illustrates an example separation device 400 that includes a plurality of separation channels 403. The separation device 400 can operate similar to a plurality of the separation channels illustrated in FIG. 2 linked together in parallel. The outputs of the separation channels can be coupled together via the manifold 107. The manifold 107 can include a first outlet for the collection of waste (or other fluid) and a second outlet for the collection of cleansed or filtered fluid. Each of the separation channels 403 can be separated from neighboring separation channels 403 by air gaps 410. The air gaps 410 can be voids in the substrates 402 and 401 that run along at least a portion of the length of the separation channel 403. The air gaps 410 can extend from the top of the top substrate 401 to the bottom of the bottom substrate 402.

The design for a separation device 400 can be based on the theory of resonant cavities. The device 400 cross section has dimensions of width and height for both the fluid-filled separation channel 403 and for the solid walls that are formed by the top layer 401 and the bottom layer 402 and define the separation channel 403. In some implementations, the acoustic force moves particles in the horizontal (e.g., the lateral or width) direction and towards a pressure node in, for example, the center of the separation channel 403. In these implementations, the analysts can place emphasis on the width dimensions. The vertical (height) dimensions can be ignored in some implementations. In some implementations, the separation channel is assumed to have a "hard wall" boundary. The hard-wall boundary can imply that a wave is approximately perfectly reflected at the boundary between fluid and solid so that the time averaged pressure P(t) attains a maximum at the fluid-solid boundary. The result of this one-dimensional, hard-wall analysis is that the fluid channel width can be one-half of an acoustic wavelength in the fluid and that the solid wall width on each side should be one fourth of an acoustic wavelength in the solid. In some implementations, multiples of one quarter are used (e.g., ½, ¾, 1 . . .). The hard wall assumption can be used to design separation channels, for example, in glass or silicon.

The term "acoustic wavelength", denoted by λ, is defined by the speed of sound c (acoustic velocity) in the material and the operating frequency ω, $$\lambda = c/\omega \tag{1}$$

Therefore, the acoustic wavelength has a specific value only for a specific property and an operating frequency, for example:

$$\lambda_f = c_f/\omega \tag{2}$$

$$\lambda_s = c_s/\omega \tag{3}$$

for the fluid and solid respectively. Since a device is ordinarily actuated at a single frequency in both fluid and solid, the above two equations can be combined as:

$$\frac{c_f}{\lambda_f} = \frac{c_s}{\lambda_s} \tag{4}$$

Further manipulation using the dimensions shown in FIG. 4A leads to a ratio of width of channel to width of wall, expressed as:

$$\frac{w_s}{w_f} = \frac{n}{2}\frac{c_s}{c_f} \tag{5}$$

$$n = 1, 2, 3, \ldots$$

and this ratio should apply for in principle for any operating frequency. Table 1 lists examples of the resulting ratio of wall width to channel width.

TABLE 1

Width of fluid channel and bounding walls and their ratios in several experiments.

| Fluid | Solid | c fluid (m/s) | c solid (m/s) | $w_f$ (mm) | $w_s$ (mm) | $w_s/w_f$ | n |
|---|---|---|---|---|---|---|---|
| saline | silicon | 1500 | 8490 | 0.377 | 1.072 | 2.84 | 1 |
| saline | silicon | 1500 | 8490 | 0.377 | 2.147 | 5.69 | 2 |
| saline | polystyrene | 1500 | 2400 | 0.430 | 1.050 | 2.44 | 3 |
| saline | polystyrene | 1500 | 2400 | 0.550 | 0.850 | 1.55 | 1.9 |

However, devices made of thermoplastics such as polystyrene cannot be accurately represented by the hard-wall approximation discussed above, and the simplified analysis does not provide appropriate design rules. Design rules for devices constructed in plastic are described below. The design rules for thermoplastics can be different because they do not call for a half wavelength in the fluid as:

$$w_f = \lambda_f/2 = \frac{c_f}{2\omega} \tag{6}$$

Instead, for separation device 400 using plastics, the channel width can be defined using design rules and dimension ratios (with respect to the wall thickness, wave speed in the fluid and plastic, and/or the operating frequency) specific to plastics. For example, the channel width can be defined as:

$$w_f \cong \lambda_f/4 = \frac{c_f}{4\omega} \tag{7}$$

which results in increased performance of driving particles to pressure nodes in separation channels 400 constructed in thermoplastics.

Table 2 compares the channel width as it relates to acoustic wavelength in both silicon and polystyrene devices (e.g., a plastic device).

| Fluid | Solid | c fluid (m/s) | c solid (m/s) | ω (MHz) | $w_f$ (mm) | $w_s$ (mm) | $\lambda_f/2$ (mm) | $w_f/\lambda_f$ |
|---|---|---|---|---|---|---|---|---|
| saline | silicon | 1500 | 8490 | 2 | 0.377 | 1.072 | 0.375 | 0.50 |
| saline | silicon | 1500 | 8490 | 2 | 0.377 | 2.147 | 0.375 | 0.50 |
| saline | polystyrene | 1500 | 2400 | 1.05 | 0.430 | 1.050 | 0.765 | 0.28 |
| saline | polystyrene | 1500 | 2400 | 0.632 | 0.550 | 0.850 | 1.187 | 0.23 |

As illustrated in Table 2, the ratio defining the channel width in a silicon device is 0.5. In contrast, for a thermoplastic device, the ratio is between 0.28 and 0.23. The ratio can be between about 0.15 and about 5, between about 0.15 and about 0.4, between about 0.2 and about 0.3, or between about 0.23 and about 0.28.

In one example, the above ratio of a thermoplastic device provides a channel with a width of 0.55 mm and a height of 0.25 mm. In some implementations, the ratio of width to height is:

$$h_f = \frac{w_f}{2.2} \quad (8)$$

Additionally, for thermoplastic based devices:

$$h_{s1} = \frac{w_s}{0.88} \quad (9)$$

$$h_{s2} = w_s/1.2 \quad (10)$$

In some implementations, the $w_s/h_{s1}$ ratio can be between about 0.5 and about 5.0, between about 0.6 and about 3.0, between about 0.7 and about 2.0, or between about 0.8 and about 1.0. In some implementations, the $w_s/h_{s2}$ ratio can be between about 0.5 and about 5, between about 1.1 and about 2, or between about 1.20 and about 1.5.

Figure 4C:
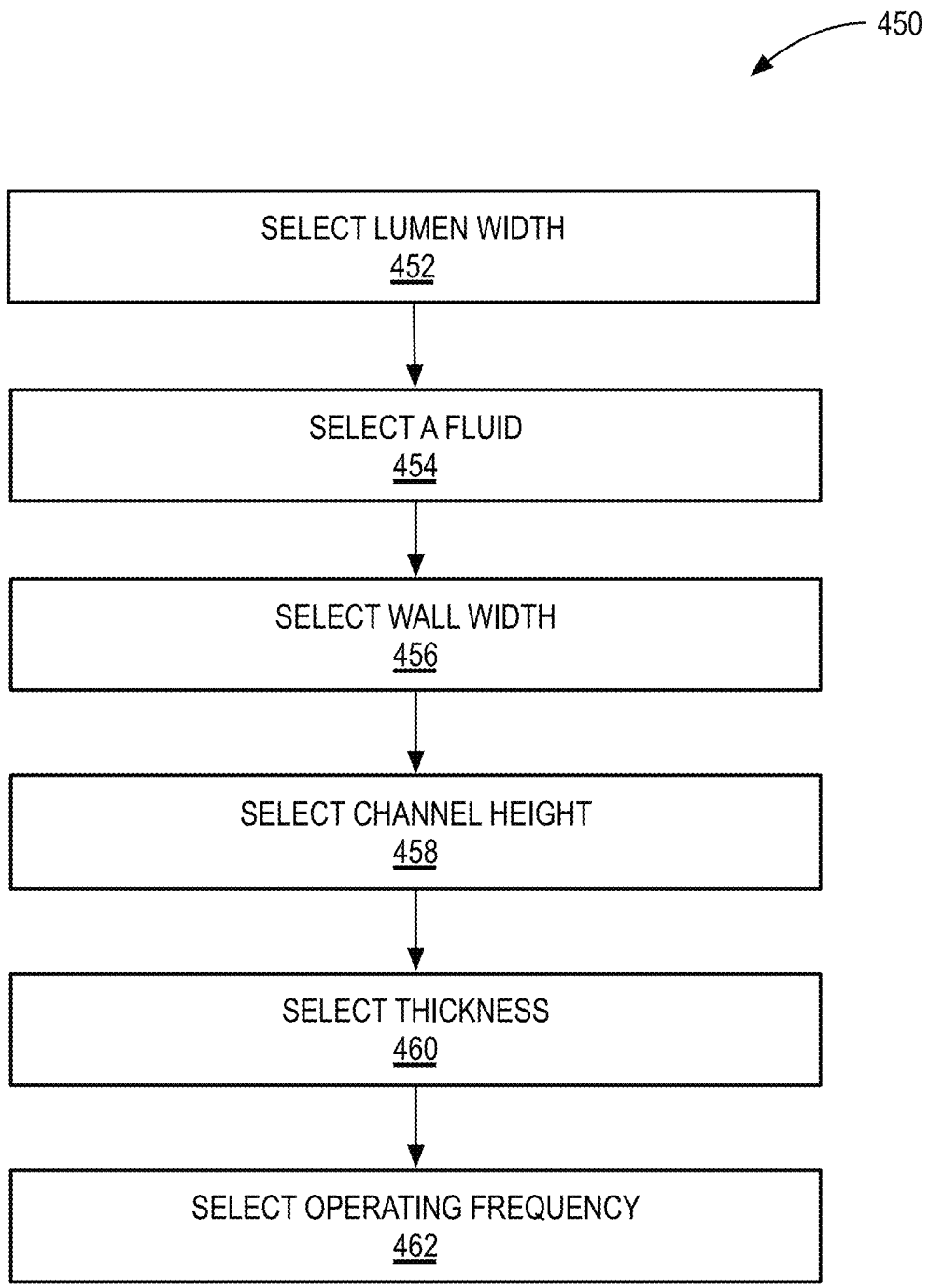
FIG. 4C illustrates a block diagram of an example method to design a separation device.

FIG. 4C illustrates a block diagram of an example method 450 to design a separation channel. The method 450 can include selecting a separation channel width (step 452). The method 450 can include selecting a fluid (step 454). The method 450 can include selecting a wall width (step 456). The method 450 can include selecting a channel height (step 458). The method 450 can include selecting a thickness (step 460). The method 450 can include selecting an operating frequency (step 462).

As set forth above, the method 450 can include selecting a separation channel width (step 452). Also referring to FIG. 4C, the method 450 can include selecting the width of the separation channel 403. The width of the separation channel 403 can be measured as the portion of the separation channel 403 parallel with the transducer 404 and the height of the separation channel 403 can be measured as the portion of the separation channel 403 perpendicular with the transducer 404. The method can include selecting the width $w_f$ of the separation channel 403. In some implementations, the separation channel width $w_f$ can be in the range of about 0.1 mm and about 5 mm, between about 0.1 mm and about 4 mm, between about 0.1 mm and about 3 mm, between about 0.1 mm and about 2 mm, or between about 0.1 mm and about 1 mm. The separation channel width can be selected first based on the desired fluid throughput of the separation device 400.

The method 450 can include selecting a fluid flow (step 454). The method 450 can include selecting which fluid to flow through the separation channel 403. The fluid can include blood. The method 450 can include determining the velocity of an acoustic wave through the fluid ($c_f$).

The method 450 can include selecting a wall width (step 456). Also referring to FIG. 4A, the wall width selected at step 456 can be the wall width $w_s$. The wall width $w_s$ can be the width of a wall perpendicular to the transducer 404. The wall width $w_s$ can be calculated according to Equation 5, with n set to 1 or 2. As illustrated in Equation 5, the wall width $w_s$ can be dependent on the separation channel width ($w_f$) selected at step 452 and the velocity of an acoustic wave through the fluid ($c_f$) selected at step 454. The wall width $w_s$ can be based on the velocity of an acoustic wave through the substrate material ($c_s$) (e.g., the velocity of an acoustic wave through the material of the substrate 402 and the substrate 401).

The method 450 can include selecting the channel height (step 458). Also referring to FIG. 4A, the channel height $h_f$ can be selected according to Equation 8, above. As illustrated in Equation 8, the channel height $h_f$ can be based on the separation channel width ($w_f$) selected at step 452. A ratio of the separation channel to the height of the separation channel can be between about 2 and about 3.5, between about 2 and about 3, between about 2 and about 2.5, or about 2.2.

The method 450 can include selecting the thickness (step 460). The method 450 can include selecting the thickness $h_{s1}$ (e.g., the floor of the separation channel 403) and the thicknesses $h_{s2}$ (e.g., the ceiling of the separation channel 403) illustrated in FIG. 4A. The thickness $h_{s1}$ can be calculated using Equation 9. The thickness $h_{s2}$ can be calculated using Equation 10. The thickness $h_{s1}$ and the thicknesses $h_{s2}$ can be calculated based on the wall width $w_s$ determined in step 456. The thickness $h_{s1}$ and the thicknesses $h_{s2}$ can be different thicknesses. In some implementations, the thickness $h_{s1}$ and the thicknesses $h_{s2}$ can be the same thicknesses. In some implementations, the thickness $h_{s1}$ of the material between the transducer 404 and the separation channel 403 can be greater than the thickness $h_{s2}$ of the substrate 401. For example, both the thickness $h_{s1}$ and the thicknesses $h_{s2}$ can be calculated using Equation 9 or Equation 10. A ratio of the wall width $w_s$ to the thickness $h_{s1}$ can between about 0.2 and about 1.5, between about 0.5 and about 1, between about 0.8 and about 1, or about 0.88. A ratio of the wall width $w_s$ to the thickness $h_{s2}$ can between about 0.75 and about 2.5, between about 1 and about 2, between about 1 and about 1.5, or about 1.2.

The method 450 can include selecting an operating frequency (step 460). Also referring to FIG. 4A, the operating frequency can be the frequency at which the transducer 404 is operated. The operating frequency can be calculated using Equation 7. The operating frequency can be calculated using the velocity of an acoustic wave through the fluid ($c_f$) selected at step 454 and the separation channel width $w_f$ selected at step 452. In some implementations, the wavelength of the operating frequency is between about 2 and about 8, between about 3 and about 6, between about 3 and about 5.5, or between about 3.3 and about 5 times the separation channel width ($w_f$).

Figure 5A:
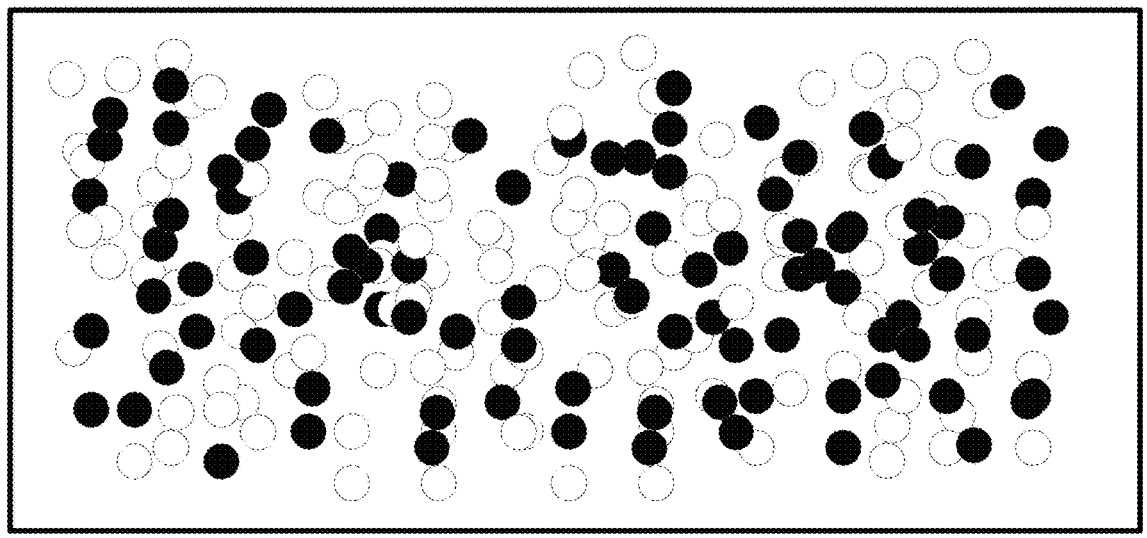
FIG. 5A is a cross sectional view of an example single-stage separation channel, as depicted in FIG. 2, containing a plurality of particles lacking an active acoustic transducer.
Figure 5B:
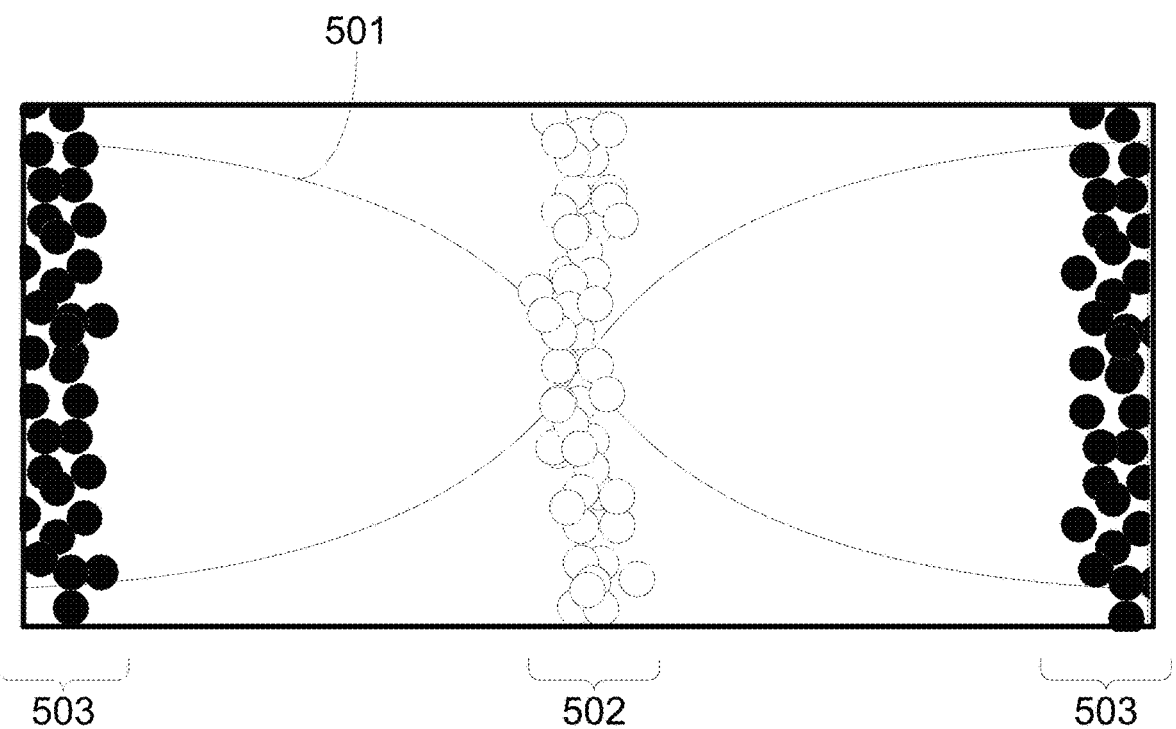
FIG. 5B is a cross sectional of an example single-stage separation channel, as depicted in FIG. 2, containing a plurality of particles adjacent to an active acoustic transducer.

FIGS. 5A and 5B are cross sectional views of particles suspended in a fluid as they flow through a separation channel similar to the separation channel 200. For FIGS. 5A and 5B, the flow of the fluid is transverse to the plane of the drawings. In some implementations, the fluid is whole blood, and the particles are the formed elements and capture particles. For illustrative purposes, FIGS. 5A and 5B contains two particles, red blood cells (white dots), and capture particles (black dots). FIG. 5A illustrates blood flowing through a channel without a standing acoustic wave being imparted on the channel and its contents. In FIG. 5A, the particles remain homogenously mixed throughout the channel. In FIG. 5B, a standing wave is imparted on the channel. The standing acoustic wave 501 creates two node types. A pressure node occurs at 502. The node extends across the full height of the lumen. The channel dimensions set forth above in relation to FIG. 4A yield a pressure node at approximately the center of the channel.

Particles are aligned based on the sign of their contrast factor. Particles with a positive contrast factor (e.g. the formed elements of blood) are driven towards a pressure node 502. In contrast, particles with a negative contrast factor (e.g. capture particles used in the single-stage device described above) are driven toward the pressure antinodes 503.

Figure 6A:
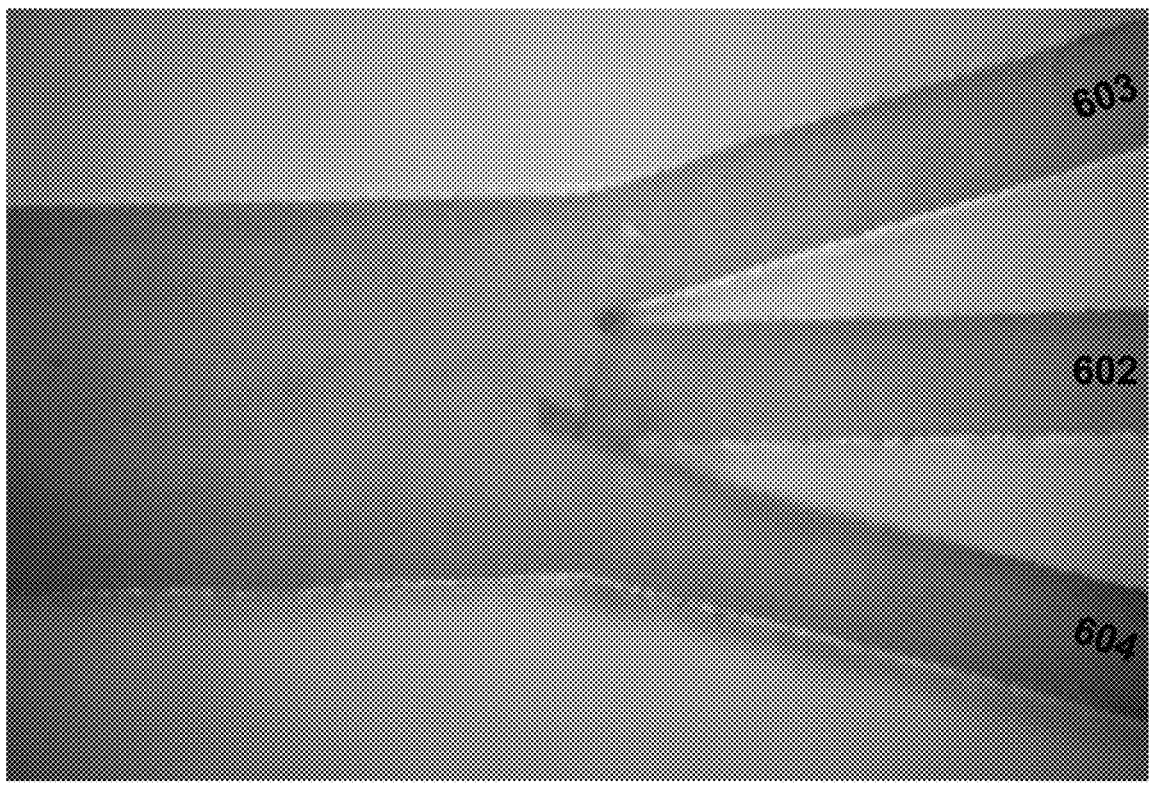
FIG. 6A is a top view of a separation channel, as depicted in FIG. 2, in which fluid is flown through the channel without the application of the standing acoustic wave.

FIG. 6A is a top view of a separation channel 600, as depicted in FIG. 2, in which fluid is flown through the separation channel 600 without the application of the standing acoustic wave. The separation channel 600 includes three outlets 602, 603, and 604. As with FIG. 5A, particles suspended in the fluid are homogeneously distributed throughout the fluid, and thus are not readily discernible in the image. The particles flow substantially evenly out of all three outlets 602, 603, and 604.

Figure 6B:
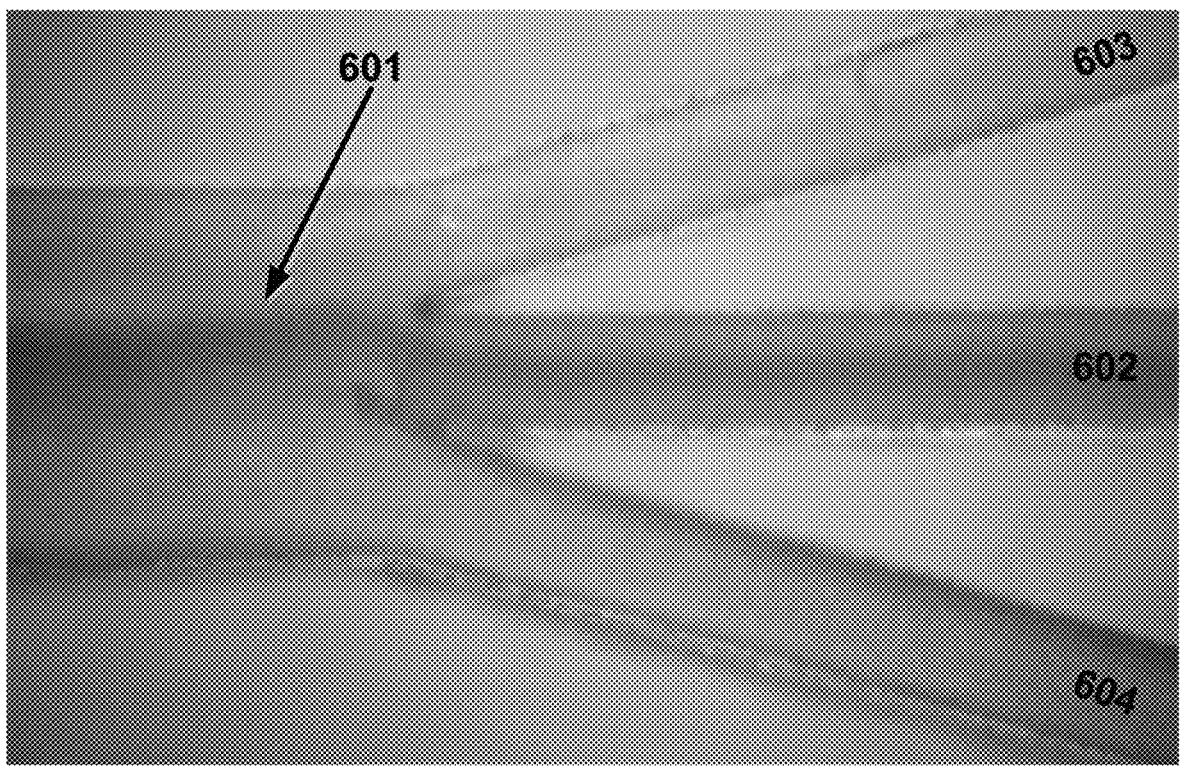
FIG. 6B is a top view of a separation channel, as depicted in FIG. 2, after the application of a standing acoustic wave.

In contrast, FIG. 6B is a top view of the separation channel 600, as depicted in FIG. 2, after the application of a standing acoustic wave, according to one illustrative embodiment.

In FIG. 6B, as a result of the standing acoustic wave, the particles 601 suspended in the fluid are aligned with the middle of the separation channel 600. Once aligned with the middle of the separation channel 600, the particles 601 exit the separation channel 600 through the middle outlet 602. The remaining fluid, substantially devoid of particles, exits the separation channel through the side outlets 603 and 604.

Figure 7:
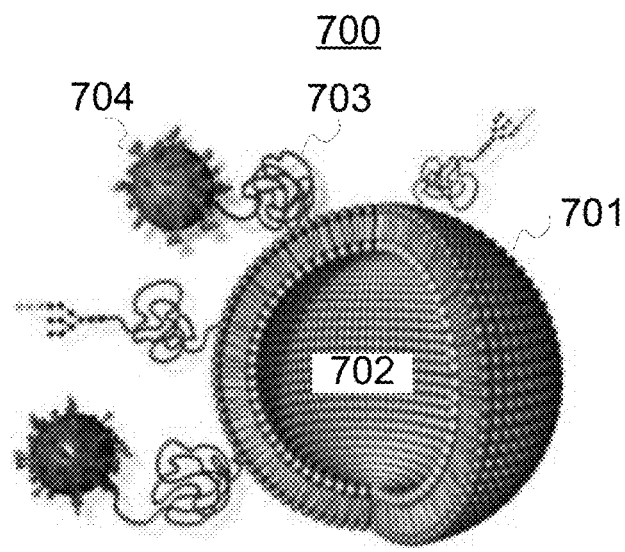
FIG. 7 is a cut away of an example lipid-based capture particle.
Figure 8A:
FIGS. 8A-8E are illustrations of the components and use for a capture particle, as depicted in FIG. 7.
Figure 8B:
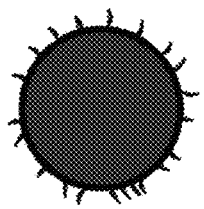
Figure 8C:
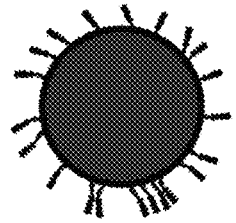
Figure 8D:
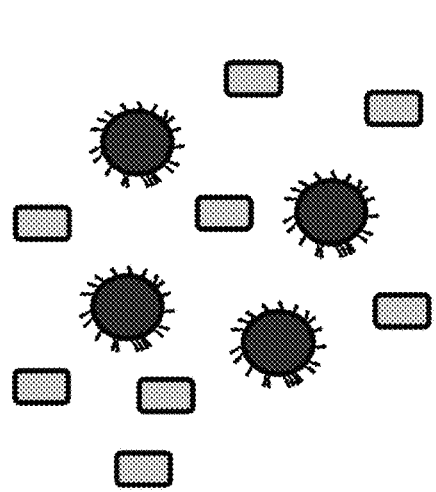
Figure 8E:
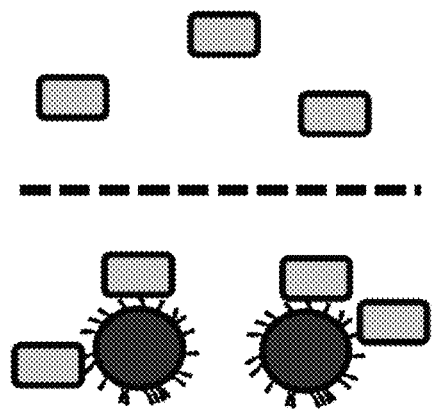

FIG. 7 is an illustrative example of a lipid bilayer capture particle 700. The capture particle 700 includes a lipid bilayer 701 encapsulating a fluid 702. Anchored in the lipid bilayer are affinity particles 703. The affinity particles bind and capture target particles 704.

More specifically, the lipid bilayer 701 forms a liposomal capture particle. In some implementations, the lipids may be, but are not limited to, dilauroyl-glycero-phosphoglycerol and dilauroyl-glycero-phosphocholine. The capture particle is tuned for acoustically induced mobility. Entities that differ in size, density, and/or compressibility have the greatest differential mobility in acoustic fields and thus are the most readily separable. Therefore, in some implementations, the size, density, and/or compressibility of the capture particles is modified to distinguish the capture particle from the formed elements of blood. The acoustic mobility of a particle is proportional to its volume. For example, in some implementations, the capture particles are about 1 µm in diameter. In other implementations, they are between about 2 and about 5 µm in diameter. In implementations that adjust the compressibility of the capture particle, the rigidity of the capture particle can be adjusted by controlling the lipid components in the bilayer. The length and saturation of the lipid hydrocarbon tail, cross-linking of the hydrophobic domains, and/or the inclusion of cholesterol can all affect the fluidity and compressibility of a liposome. In other implementations, the density of the liposome is engineered by encapsulating an acoustically active fluid 702. In these implementations, the acoustical active molecule can be an FDA-approved contrast agent, glycerin, castor oil, coconut oil, paraffin, air, and/or silicone oil. In other implementations, all the above described characteristics are manipulated to create a capture particle with the greatest possible difference in contrast factor compared to a formed element.

As described above, the acoustically induced mobility of a particle is based on the contrast factor of the particle. For a liposomal based capture particle, the contrast factor is dominated by the properties of the encapsulated fluid. The contrast factor is based on the bulk modulus (K) and density ($\Psi$) of the encapsulated fluid. When suspended in blood, the contrast factor ($\perp$) for a capture particle, encapsulating a specific fluid, is calculated with the below equation:

$$\varphi = \frac{5\rho - 2 \cdot 1.02}{2\rho + 1.02} + \frac{2.2}{K} \quad (11)$$

Table 4 provides the $\Psi$, K, and then calculated $\perp$-factor based on the above equation.

TABLE 4

| | Calculated Contrast Factors | | | |
|---|---|---|---|---|
| | Materials | $\Psi$ (g/ml) | K(Gpa) | $\perp$ |
| Encapsulated Fluids | glycerin | 1.25 | 4.7 | +0.73 |
| | castor oil | 1.03 | 2.06 | −0.06 |
| | coconut oil | 0.92 | 1.75 | −0.36 |
| | paraffin | 0.80 | 1.66 | 0.58 |
| | silicone oil | 1.04 | 1.09 | −1.00 |
| | air | 0.002 | 1.4 | −3.55 |
| Formed Elements | white blood cell | 1.02 | 2.5 | +0.12 |
| | red blood cell | 1.10 | 3.0 | +0.34 |

In some implementations, such as the implementation of FIG. 3, the capture particles have a contrast factor that is lower in magnitude, but still of the same sign as the formed elements. In these implementations, the low contrast factor of the capture particles can be achieved by making the capture particles sufficiently small to reduce their contrast factor to below that of the formed elements.

As illustrated in FIG. 7, affinity molecules 703 are embedded in the lipid bilayer 701. In some implementations, these affinity molecules are glycoconjugates. The glycoconjugates enable the capture and retention of all major classes of pathogens, including bacteria and viruses. In some implementations, the affinity molecules 703 also bind to toxins and pro-inflammatory cytokines. In some implementations, affinity molecules 703 are designed to universally capture gram-negative and gram-positive bacteria, viruses, and toxins, by exploiting that: 1) pathogens express unusual surface N- and O-linked glycan structures that can be targeted by glycan-binding proteins or lectins and 2) many pathogens and toxins bind to charged polysaccharides, especially those of the heparan sulfate family, that are present on the cell surface of mammalian cells. Some implementations employ glycoconjugate capture agents that have two components: a modified, non-anticoagulant heparin fragment that nevertheless maintains high affinity, multivalent binding properties, and a glycan-binding protein that binds to surface N- and O-linked glycans present on the surface of pathogens. In other implementations, the glycan structure is a lectin. For example the lectin can be, but is not limited to: type 2 membrane receptors such as DC-SIGN, DC-SIGNR, and Langerine; collectins such as pulmonary surfactant proteins (SP-D, SP-Al), mannose binding lectin, and collectin-Kl; and macrophage mannose receptors. In other implementations, the affinity molecule is an antibody.

The affinity particles are anchored to the liposomal surface so their concentration, valency, and distribution can be controlled. This is particularly relevant since pathogen-receptor interactions are often multivalent and the receptor configuration impacts overall avidity. In some implementations, the affinity molecule is attached to an anchor that is incorporated into the lipid bilayer, so the embedded functional groups remain in close proximity but are free to rotate and rearrange. Lipid anchors are favored because the molar ratio of derivatized lipids incorporated can be controlled. Lectins are incorporated by solubilizing a surfactant with pre-formed liposome suspensions, through direct addition of fatty acids to lysine residues, or by modification with hydrophobic anchor lipids such as Nglutaryl-phosphotidy-lethanolamine (NGPE).

FIG. 8 illustrates an overview of the process of making and using a capture particle. The affinity molecules of FIG. 8A are embedded in the liposome of FIG. 8B to produce an affinity coated liposome as illustrated in FIG. 8C. Next, the capture particles are combined with a blood or other fluid containing target particles. The target particles then bind to the capture particles. FIG. 8E illustrates, bound target particles can then be removed from the fluid by acoustically moving the capture particles whereas unbound target particles are not removed from the fluid.

Figure 9:
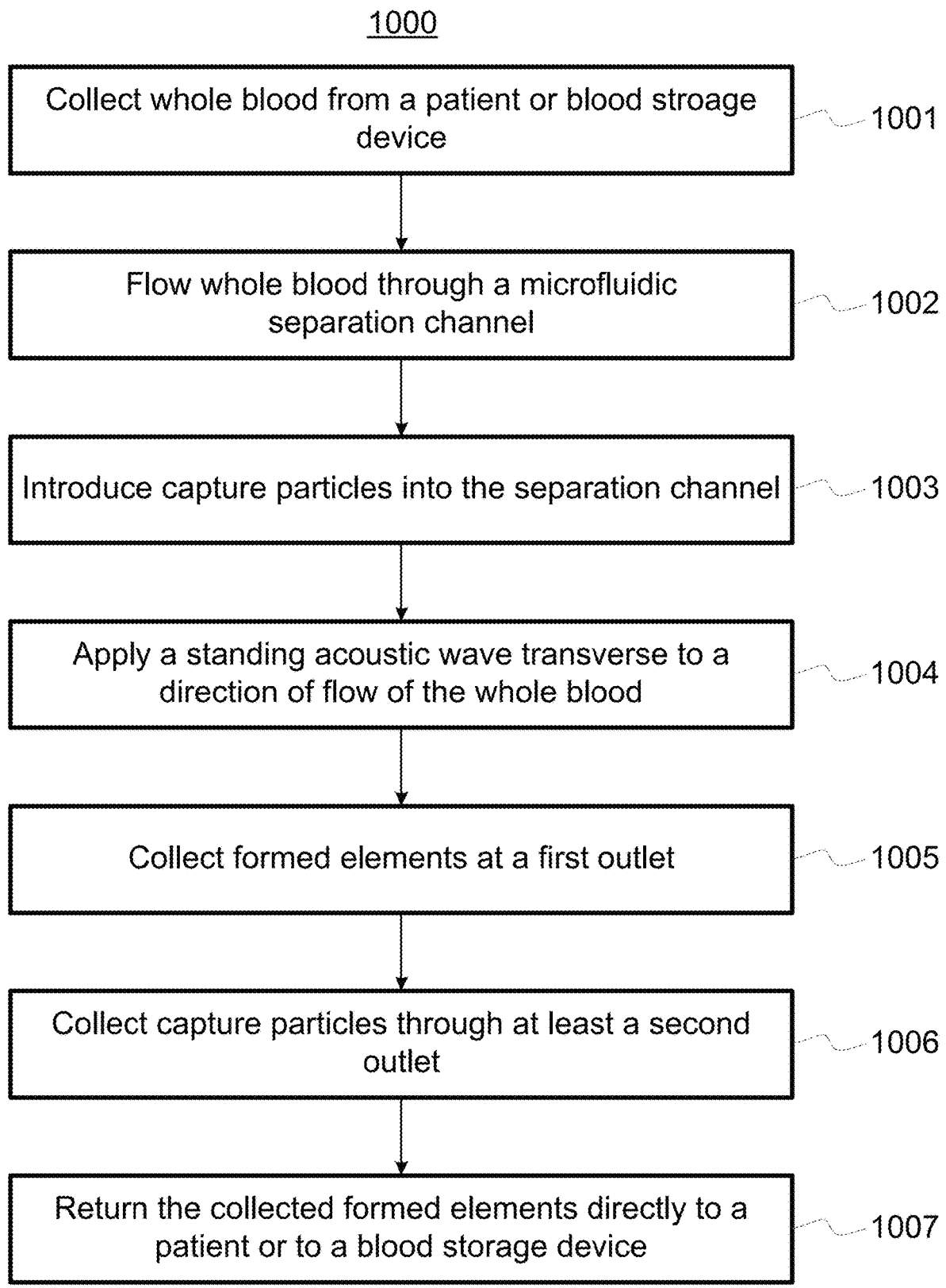
FIG. 9 is a flow chart of an example method for cleansing blood with a single-stage separation channel, as depicted in FIG. 2.

FIG. 9 is a flow chart of a method for cleansing blood with a single-stage microfluidic separation channel (1000). First, whole blood is collected (step 1001). Then whole blood is flowed into an inlet of a single-stage microfluidic separation channel, as depicted in FIG. 2 (step 1002). Next, a plurality of capture particles is introduced into the whole blood (step 1003). Then a standing acoustic wave is applied to the separation channel (step 1004). The formed elements are then collected in a first outlet (step 1005). Next, the capture particles are collected in a second outlet (step 1006). Finally, the cleansed blood is returned to a storage container or returned directly to the patient (step 1007).

Referring to FIGS. 1, 2, and 10, the method 1000 of cleansing blood with a single-stage microfluidic separation channel 200 begins by collecting whole blood. In some implementations, the whole blood is collected from a patient 101, and then directly introduced into the blood cleansing system 100. In other implementations, the whole blood is collected from a patient 101 and then stored for later cleansing.

The method 1000 of cleansing blood with a single-stage microfluidic separation channel 200 continues by flowing whole blood into the inlet of a microfluidic separation channel (step 1002). The whole blood contains a plurality of formed elements, plasma, and a plurality of target particles. In some implementations, the target particles can be toxins, bacteria, and/or viruses. In some implementations, a single microfluidic separation channel is used, while in others a plurality of single-stage separation channels is used in conjunction to accommodate greater blood flow throughput.

The method 1000 can include introducing a plurality of capture particles into the whole blood (step 1003). In some implementations, the constituent components of capture particles are injected into a separation channel with a micronozzle and spontaneously form capture particles as injected into the separation channel. In other implementations, the capture particles are prefabricated and then introduced into the whole blood. In some implementations, the capture particles are introduced into the whole blood after the whole blood enters the separation channel through the first inlet 202. In yet other implementations, the capture particles are introduced into the whole blood before the blood enters through the first inlet 202 of the separation channel 200. In some implementations, the capture particles are microbeads and/or lipid based liposomes.

The method 1000 includes applying a standing acoustic wave to the separation channel (step 1004). The standing acoustic wave is applied transverse to a direction of flow of the whole blood through the separation channel 200. In some implementations, the formed elements and capture particles have contrast factors with different signs. Thus, the application of the standing acoustic wave causes the formed elements to aggregate about the central axis of the separation channel and the capture particles to aggregate along at least one wall of the separation channel, as depicted in FIG. 2. In other implementations, the standing acoustic wave causes the formed elements to aggregate along at least one wall of the separation channel and the capture particles to aggregate about the central axis of the separation channel.

The method 1000 can include collecting the formed elements of the whole blood in a first outlet (step 1005). In some implementations, as depicted in FIG. 2, a first outlet 204 is aligned with the central axis of the separation channel allowing the outlet to collect the formed elements as they aggregate and flow down the central axis of the separation channel. Similarly, the method continues with the collecting of the capture particles in a second outlet (step 1006). In some implementations, the end of the separation channel has at least a second outlet channel 206 and 207 aligned with at least one wall of the separation channel. As the capture particles are driven towards the antipressure notes along the walls of the separation channel, they are collected by the outlets channels 206 and 207 aligned with the walls of the separation channels. In some implementations, the standing acoustic wave is adjusted such that the formed particle aligns along the walls of the separation channel and the capture particles align with the central axis of the separation channel. In such an implementation, the formed elements are funneled into outlets along the wall of the separation channel and the capture particles are funneled into an outlet aligned with the central axis of the separation channel. In some implementations, the outlet channels 206 and 207 terminate in individual outlets or merge to terminate into a single outlet 205.

The method 1000 can include the reintroduction the cleansed blood into a patient 101 or storage (step 1007). In some implementations, such as system 100, the whole blood is collected directly from a patient and then reintroduced to the patient 101. In some implementations, the cleansed blood is reheated to body temperature before being reintroduced into the patient 101. In other implementations, the cleansed blood is collected in a storage container for later reintroduction into a patient 101.

The plastic-based devices described herein can be used to separate acoustically active particles from fluids. The devices described herein can be used with or without capture particles. For example, particles and cells (e.g., target particles) can be removed from a fluid based on the target particles' acoustic properties with respect to the fluid in which they are contained. The fluids can be biological based (e.g., a bodily fluid such as blood) or non-biological based (e.g., waste water). In one example, the plastic-based devices described herein can be used in the isolation of natural blood cells such as hematopoietic stem cells or T-lymphocytes. The device can be used in cell therapy and bioprocessing. For example, the device can separate out hematopoietic stem cells or T-lymphocytes based on their acoustic activity with respect to the fluid (e.g., blood) flowing through the device. The hematopoietic stem cells or T-lymphocytes can be driven to an aggregation axis at a rate different than the other elements in the fluid enabling the hematopoietic stem cells or T-lymphocytes to be separated from the fluid at different points along the length of the device. In other implementations, debris or other target particles can be removed from fluid flowing through the device. For example, the particles or debris can be removed from large scale batches of cultured cells (e.g. mesenchymal stem cells) prior to therapeutic injection of such cells.

In some implementations, the plastic-based devices described herein can be used in antibiotic susceptibility testing. For example, the device can be a component of a system for bacterial identification that can include a single, self-contained, point-of-care or lab-based diagnostic system. The system can be used to detect foreign agents, such as bacteria, within blood or other samples. The system can receive as input the blood or other samples and output an indication of whether, and to what degree, the foreign agent is present in the sample. The system can reduce the time scale for bacteria detection to a few hours and serve as a point-of-care diagnostic tool within hospital, lab, and other medical facilities. The system can include disposable microfluidic cartridges that include the plastic-based separation device that are removable from the system and can be replaced between tests. The microfluidic cartridges can receive a sample, such as a blood sample, that is suspected of containing bacterial cells and separate the bacterial cells from the blood sample. Once the bacterial cells are separated from the blood, the system can introduce recombinant detector phages (RDBs) into the system. The RDB can include one or more reporter genes. When the RDB comes into contact with a specified bacterial cell type, the RDB can infect the bacterial cells with the reporter gene. Once infected, the bacterial cells can then express the reporter gene. The system can detect a signal generated responsive to the expression of the reporter gene with an optical detector. The signal can include luminescence, fluorescence, or chromagraphic signals generated in response to the expressed reporter gene. The system can display or otherwise report out the signal as an indication of the presence of the foreign agent. Additional information of a bacterial identification system can be found in U.S. patent application Ser. No. 15/470,750, which is incorporated by reference in its entirety.

EXAMPLES

Different separation channels were constructed in thermoplastics to test and illustrate the improved performance of devices designed using the techniques described herein, such as the method 450. The performance of the channels using the herein described methods was measured using the prominence of local maxima. Prominence can have the advantage over raw pixel intensity for the purposes of comparison due to its self-normalizing nature. Since prominence is measured relative to points on the signal itself it is robust against irregularities inherent to the signal. These irregularities can take the form of variable lighting conditions between experimental runs, such as variations in environmental lighting, and illumination variabilities within a single microscope image's region of interest, such as skewed background intensities caused by shadows.

Peak prominence is used as a direct measure of merit for device screening studies in which the assumption of a functional geometry (e.g., a geometry capable of focusing particles) cannot be made. When a device is determined to function well based on its prominence score it is compared to the baseline geometry using the ratio of peak prominence to half-prominence width, $\chi$. $\chi$ cannot be used during device screening as the metric can skew results by rewarding peaks with relatively small prominence values and correspondingly small widths. However, this metric is useful for comparing the quality of the most prominent peaks among different, commensurate, devices such as the winner of a design screening iteration and the baseline geometry.

A device's performance can be tested head-to-head against the baseline geometry using the full, trifurcated, designs shown in FIG. 2. The performance testing can include comparing each design's ability to focus blood to the center channel, as shown in FIG. 2, as well as each design's ability to separate bacteria from blood.

The half-prominence width of a peak of prominence Prom is calculated by drawing two horizontal lines extending in the negative and positive directions from the point of half-prominence. These lines extend in either direction until either the end of the signal is reached or the line intersects the signal itself. The indices of these events in the negative and positive directions are recorded as $i^-$ and $i^+$, respectively. The peak width Half Prom Width is then defined as $|i^+ - i^-|$. The final equation for $\chi$:

$$\chi = Prom * \frac{W_c}{\text{Half Prom Width}} \quad (12)$$

Figure 10A:
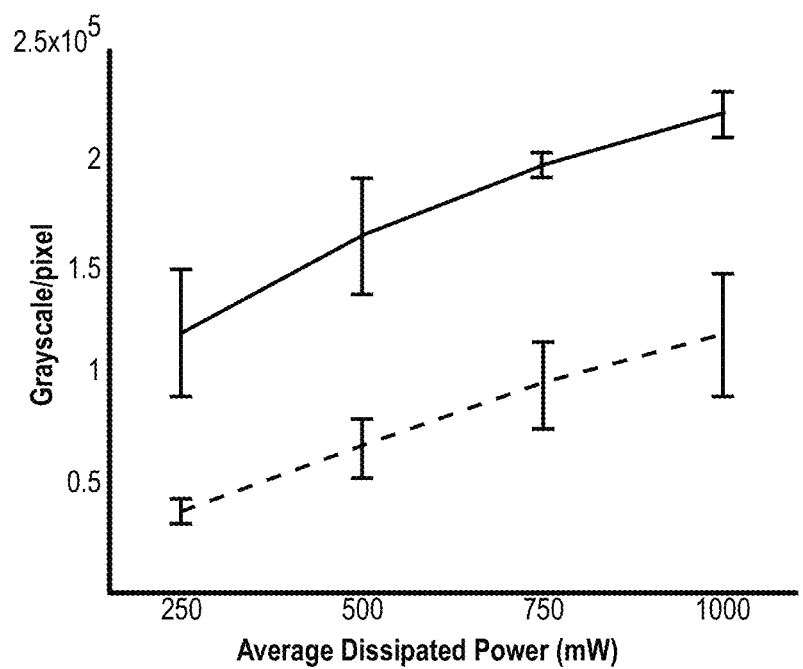
FIGS. 10A-10C illustrate plots of the performance of separation devices at several flow rates using the design rules described herein and baseline devices, in terms of each device's ability to focus red blood cells to a central aggregation axis.
Figure 10B:
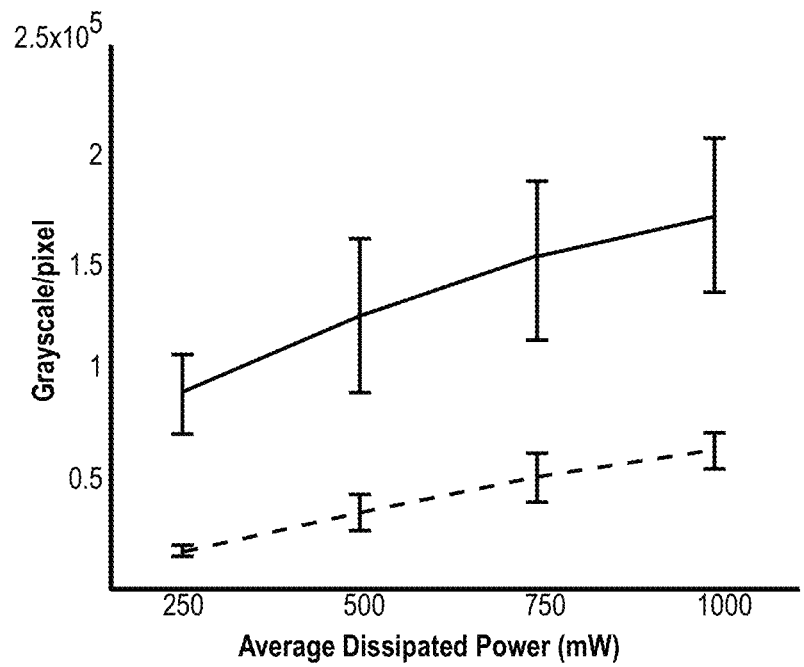
Figure 10C:
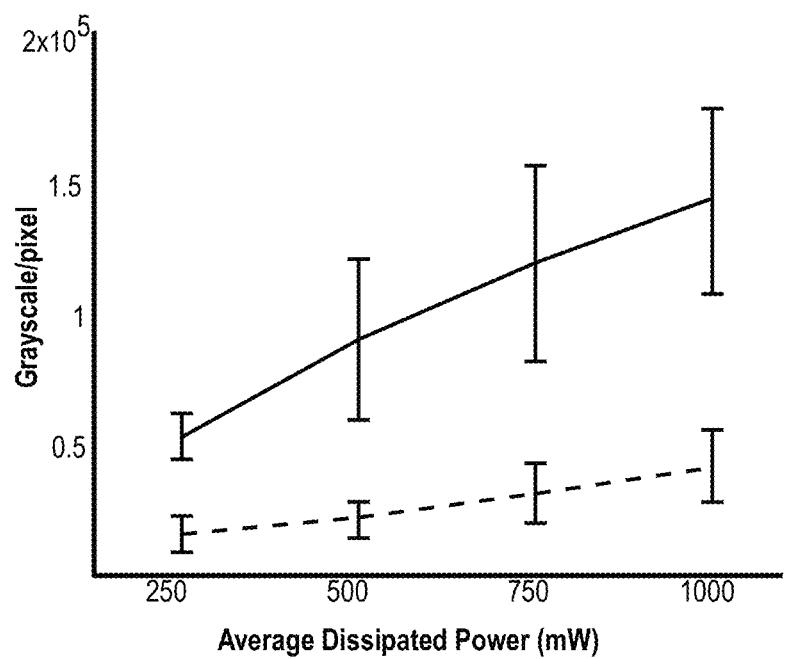

Constructing a separation channel using the above formulas for a thermoplastic device, a separation channel with a channel width of 550 μm, a channel height of 250 μm, a side-wall width of 850 μm was constructed (and is referred to as the experimental design). This experimental device was compared against a baseline device using the dimensions as illustrated in FIG. 3. The comparison of the performance of the separation device is illustrates in FIGS. 10A-10C. The solid line illustrates the normalized prominence vs average dissipated power (mW) of the experimental device constructed using the equations for a thermoplastic device and the dashed line illustrates the normalized prominence of the baseline device. FIG. 10A illustrates the operation of the devices with a 25 μl/min flow rate, FIG. 10B with a 50 μl/min flow rate, and FIG. 10C with a 75 μl/min flow rate. As illustrated in FIGS. 10A-10C, the normalized prominence (indicating a grayscale/pixel) is greater at each average dissipated power level and at each of the tested flow rates for the experimental device than for the baseline device. The prominence can indicate the ability of the device to concentrate particles near the middle of the separation channel. Accordingly, FIGS. 10A-10C illustrate that the experimental device was better able to focus particles near the middle of the separation channel when compared to the baseline device.

Figure 11A:
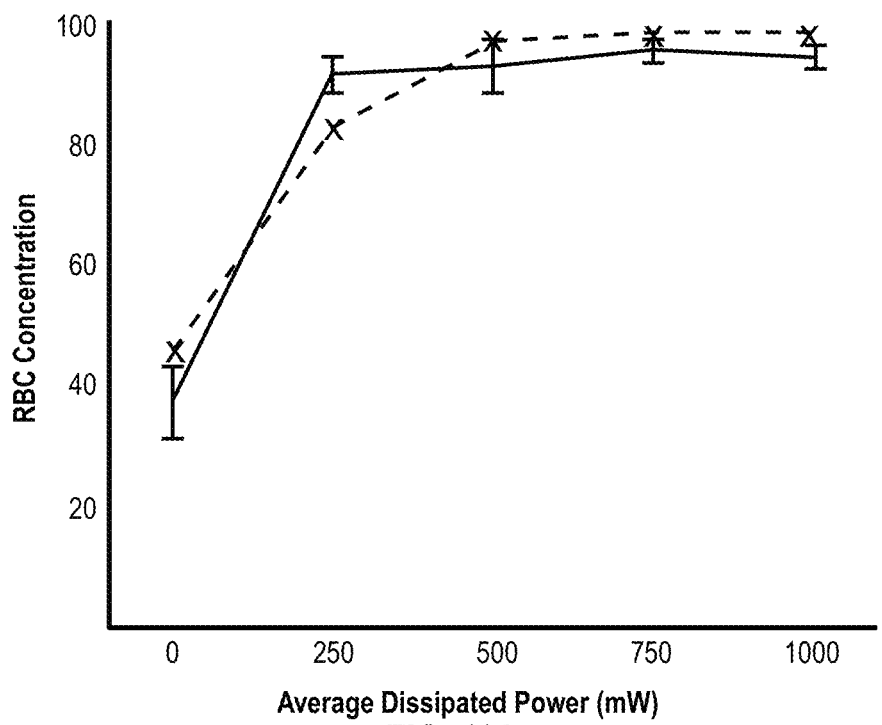
FIGS. 11A-11C illustrate plots of the performance of the experimental device against the baseline in terms of each device's ability to focus red blood cells to a central aggregation axis and out a center outlet port.
Figure 11B:
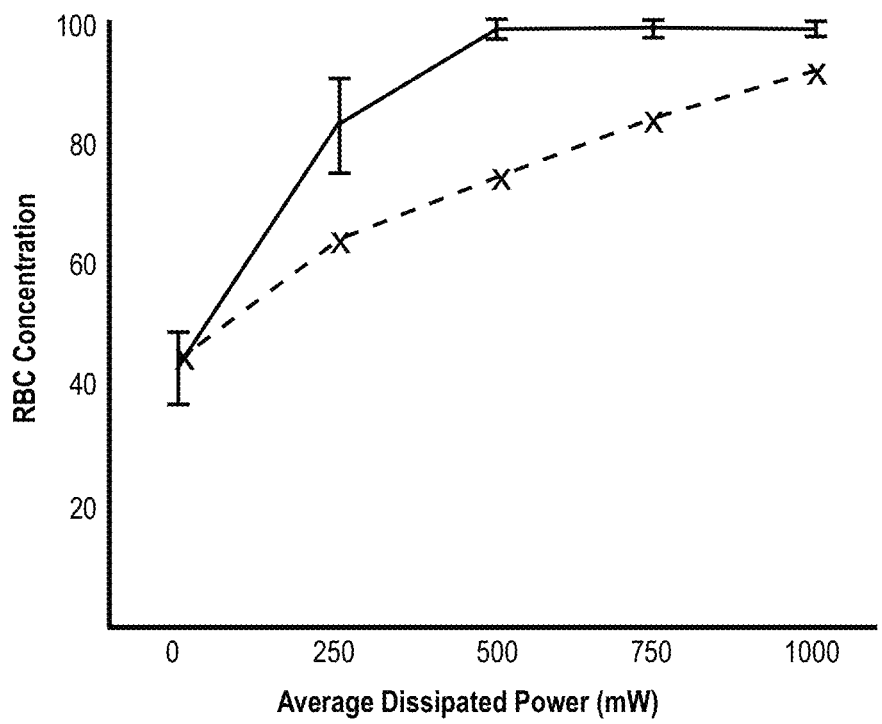
Figure 11C:
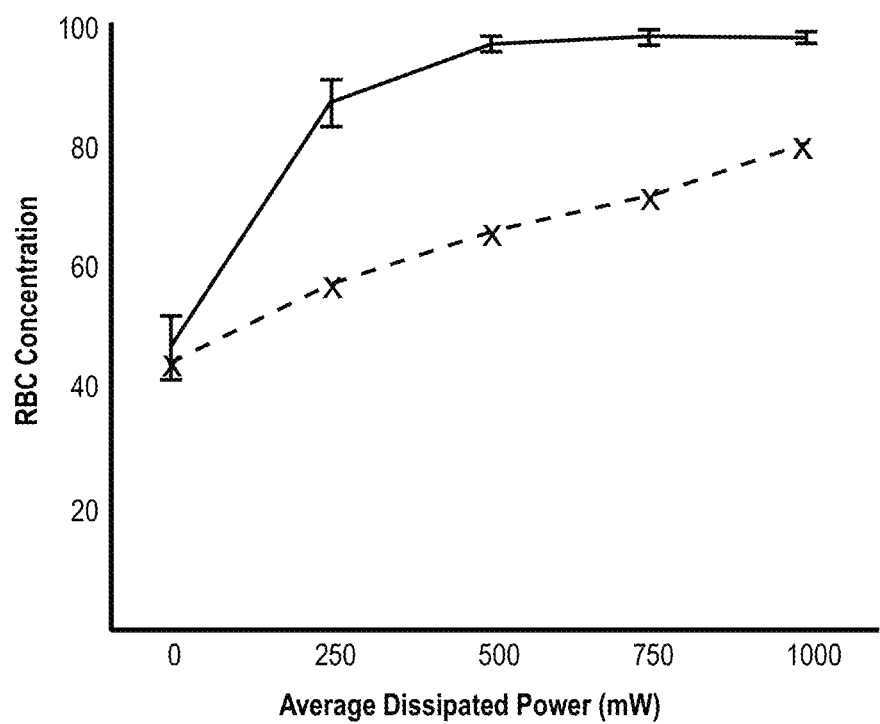

FIGS. 11A-11C illustrate plots of the performance of the experimental device against the baseline in terms of each device's ability to focus (e.g., divert) red blood cells (RBC) to a central aggregation axis. The dynamic range of each measurement was limited to that which falls between the performance at the control measurement (e.g., zero average dissipated power) and 100% RBC concentration in the center channel. As the chip design used, shown in FIG. 2, has a single input port and two outlet ports, RBCs will be equally distributed between the two outlet ports in the acoustics-off (0 W input power) condition.

In FIGS. 11A-11C the solid lines indicate the RBC concentration exiting the center channel of the experimental device at each of a plurality of different dissipation powers. The dotted lines indicate the RBC concentration exiting the center channel of a baseline device at each of a plurality of different dissipation powers. The baseline and experimental design demonstrated comparable performance at a flow rate of 25 μl/min across all power settings (FIG. 11A); however, at higher flow rates (e.g., 50 μl/min in FIG. 11B and 75 μl/min in μl/min FIG. 11C) the experimental design outperformed the baseline across all non-control power settings as illustrated by the experimental device's central channel having a higher RBC concentration.

Additionally, four experiments were conducted, two for each device design (baseline and experimental), in order to determine the optimal value for each measure of merit while holding the other constant. Optimality was defined as the maximum flow rate or minimum power required to maintain 90% RBC separation between the side and center ports while achieving equivalent bacteria-blood separation performance.

Figure 12A:
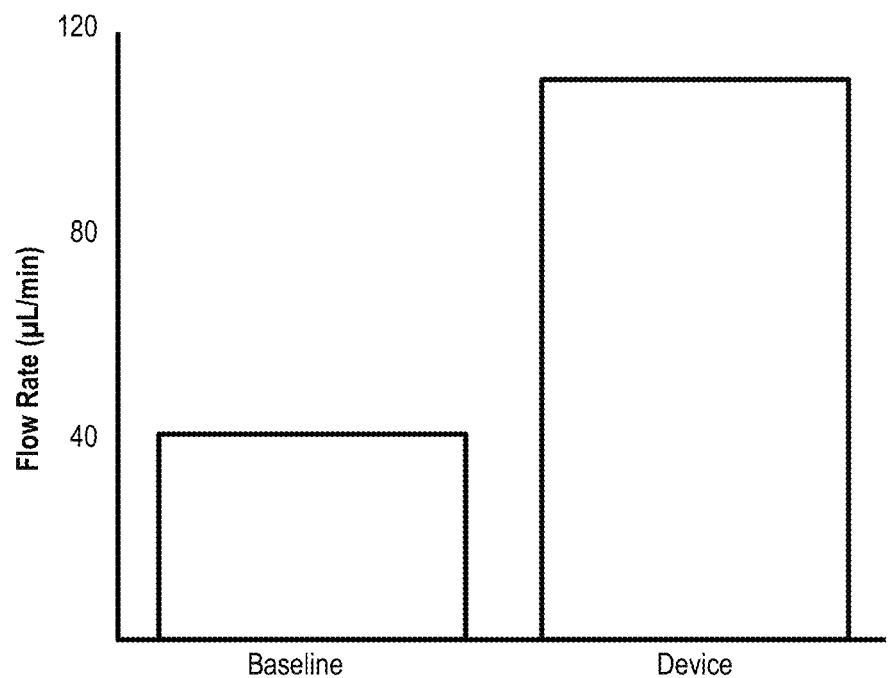
FIG. 12A illustrates the relative performance of the baseline device as it compares to the experimental design in terms of flow rate with power held constant at 1 W.
Figure 12B:
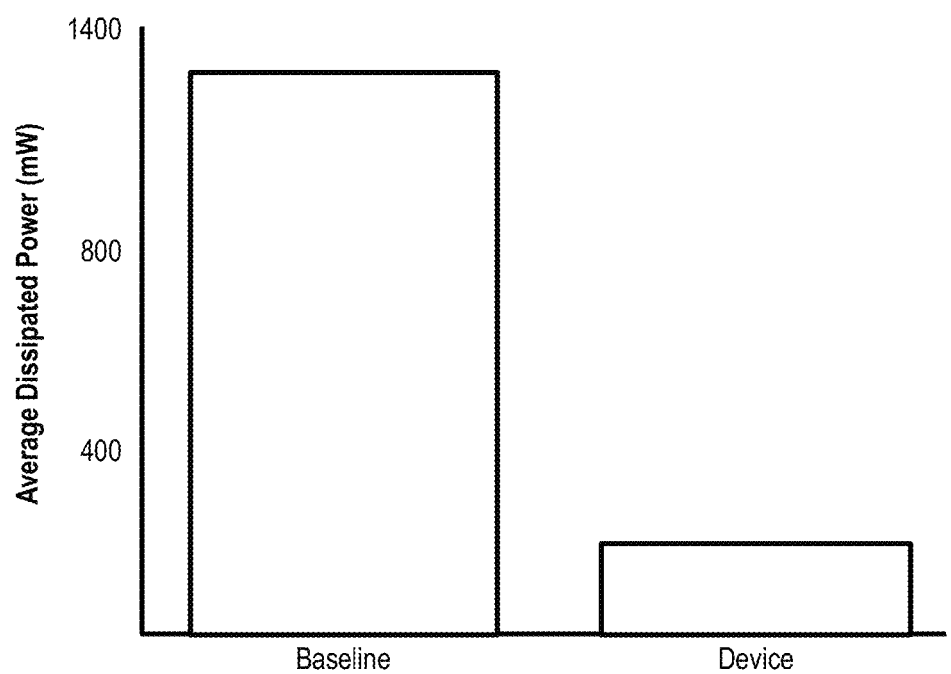
FIG. 12B illustrates the performance of the experimental design and baseline design when holding flow rate at 50 µL/min while varying power.

FIG. 12A illustrates the relative performance of the baseline device as it compares to the experimental design in terms of flow rate with power held constant at 1 W. Each of the devices are performing comparable separation of bacterial cells from blood. FIG. 12B illustrates the performance of the two chip designs holding flow rate at 50 μL/min while varying power. Each of the devices are performing comparable separation of bacterial cells from blood. Constant values were maintained for RBC separation and bacterial recovery for all chip designs and experiments FIG. 12A illustrates that the experimental design achieved a 175% increase in throughput relative to the baseline design. Additionally, the experimental design was able to decrease the average dissipated power by 81.63% when compared to that of the baseline geometry. The actual average RBC separation across all four experiments was 95.25% (±1.89%). The purity of the bacterial samples collected at the side port had a standard deviation of 0.05%. Additionally, the experimental design achieved better RBC separation and equivalent bacterial recovery relative to the baseline for both the maximum flow rate and minimum power experiments (98% vs 94% and 95% vs 94%, respectively).

What is claimed:

1. A device, comprising:
    an acoustic transducer;
    a separation channel configured to carry a fluid and defined within a first thermoplastic substrate forming a first sidewall, a second sidewall, and a roof of the separation channel, the first thermoplastic substrate coupled with a second thermoplastic substrate forming a floor of the separation channel, the floor configured to couple with the acoustic transducer, wherein:
        a first width of the separation channel is selected to be between 0.2 and 0.3 times an acoustic wavelength of a first acoustic wave imparted in the fluid by the acoustic transducer;
        the first sidewall and the second sidewall each have a second width selected based on the first width of the separation channel, a velocity of the first acoustic wave imparted in the fluid, and a velocity of a second acoustic wave imparted on the first thermoplastic substrate; and
    a first inlet defined within the first thermoplastic substrate to introduce the fluid into a proximal end portion of the separation channel;
    a first outlet defined within the first thermoplastic substrate, the first outlet positioned at a downstream portion of the separation channel substantially along a longitudinal axis of the separation channel; and
    a second outlet defined within the first thermoplastic substrate, the second outlet positioned at the downstream portion positioned adjacent to a first sidewall of the separation channel.

2. The device of claim 1, wherein the floor has a second thickness determined by the first width of the separation channel.

3. The device of claim 1, wherein the first width of the separation channel is between 0.1 mm and 3 mm.

4. The device of claim 1, wherein a wavelength of an acoustic wave generated by the acoustic transducer is between about 3.3 and about 5 times the first width of the separation channel.

5. The device of claim 1, wherein a height of the separation channel is determined by the first width of the separation channel.

6. The device of claim 1, wherein a ratio of the first width of the separation channel to a height of the separation channel is between 2 and 2.5.

7. The device of claim 1, wherein the floor of the separation channel has a second thickness different from a first thickness of the roof of the separation channel.

8. The device of claim 1, wherein the second thickness is greater than the first thickness.

9. The device of claim 1, wherein a ratio of a thickness of the floor of the separation channel to the first width of the separation channel is between about 0.5 and 1.

10. The device of claim 1, further comprising a plurality of separation channels defined within the first thermoplastic substrate, each of the plurality of separation channels separated by an air gap.

11. A method to process fluid, comprising:
    providing a separation device comprising:
        an acoustic transducer;
        a separation channel configured to carry a fluid and defined within a first thermoplastic substrate forming a first sidewall, a second sidewall, and a roof of the separation channel, the first thermoplastic substrate coupled with a second thermoplastic substrate forming a floor of the separation channel, the floor configured to couple with the acoustic transducer, wherein:
            a first width of the separation channel is selected to be between 0.2 and 0.3 times an acoustic wavelength of a first acoustic wave imparted in the fluid by the acoustic transducer;
            the first sidewall and the second sidewall each have a second width selected based on the first width of the separation channel, a velocity of the first acoustic wave imparted in the fluid, and a velocity of a second acoustic wave imparted on the first thermoplastic substrate; and
        a first inlet defined within the first thermoplastic substrate to introduce the fluid into a proximal end portion of the separation channel;
        a first outlet defined within the first thermoplastic substrate, the first outlet positioned at a downstream portion of the separation channel substantially along a longitudinal axis of the separation channel; and a second outlet defined within the first thermoplastic substrate, the second outlet positioned at the downstream portion positioned adjacent to a first sidewall of the separation channel;

flowing a target fluid through the first inlet, wherein the target fluid comprises target particles; and driving, with a standing acoustic wave generated by the acoustic transducer, the target particles toward the first sidewall of the separation channel.

12. The method of claim 11, wherein the first width of the separation channel is between 0.1 mm and 3 mm.

13. The device of claim 1, wherein the roof has a first thickness selected such that a ratio of the first thickness of the roof to the first width of the first sidewall and the second sidewall is between 1.1 and 2.0.

14. The method of claim 11, wherein a height of the separation channel is based on the first width of the separation channel.

15. The method of claim 11, wherein a ratio of the first width of the separation channel to a height of the separation channel is between 2 and 2.5.

16. The method of claim 11, wherein the floor of the separation channel has a second thickness that is greater than a first thickness of the roof of the separation channel.

17. The method of claim 11, wherein a ratio of a second thickness of the floor of the separation channel to the first width of the separation channel is between about 0.5 and 1.

18. The method of claim 11, wherein the roof has a first thickness selected such that a ratio of the first thickness of the roof to the first width of the first sidewall and the second sidewall is between 1.1 and 2.0.

* * * * *